United States Patent
Lunn et al.

(10) Patent No.: US 10,765,420 B2
(45) Date of Patent: Sep. 8, 2020

(54) SUTURE PASSER

(71) Applicant: Smith & Nephew, Inc., Memphis, TN (US)

(72) Inventors: Richard M. Lunn, Kingston, MA (US); Paul Alexander Torrie, Marblehead, MA (US); Timothy Young, Natick, MA (US); John Albert Slusarz, Jr., Memphis, TN (US); Geoffrey Ian Karasic, Milton, MA (US); Amanda Simard, Hopkinton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 273 days.

(21) Appl. No.: 15/306,406

(22) PCT Filed: Apr. 24, 2015

(86) PCT No.: PCT/US2015/027640
§ 371 (c)(1),
(2) Date: Oct. 24, 2016

(87) PCT Pub. No.: WO2015/164819
PCT Pub. Date: Oct. 29, 2015

(65) Prior Publication Data
US 2017/0042533 A1    Feb. 16, 2017

Related U.S. Application Data

(60) Provisional application No. 61/983,487, filed on Apr. 24, 2014.

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0483* (2013.01); *A61B 17/06004* (2013.01);
(Continued)

(58) Field of Classification Search
CPC .......... A61B 17/0469; A61B 17/06109; A61B 17/0483; A61B 17/06004;
(Continued)

(56) References Cited

U.S. PATENT DOCUMENTS 17,272 A    5/1857    Garvey
349,791 A   9/1886    Gibboney, Jr.
(Continued)

FOREIGN PATENT DOCUMENTS

CN    201930033 U    8/2011
DE    245573 C       4/1912
(Continued)

OTHER PUBLICATIONS

Gardner, R.C. (1975), The Hand, "A Malleable Needle for Tendon Surgery," pp. 185-186.
(Continued)

*Primary Examiner* — Phong Son H Dang
(74) *Attorney, Agent, or Firm* — Burns & Levinson, LLP; Joseph M. Maraia

(57) ABSTRACT

The present disclosure concerns a surgical instrument for manipulating suture. In particular, the present disclosure relates to an instrument for passing suture through tissue. There is described a surgical instrument having a shaft and a handle connected to the proximal end of the shaft. The shaft is formed from a tubular member having a proximal end and a distal end, with a lumen extending between the proximal and distal ends, and a tip distal to the tubular member. The shaft also includes a distal portion having an opening in a sidewall, proximal to the tip. The opening is in
(Continued)

communication with the lumen through a side channel. The instrument further includes a suture snare, the snare being slidably receivable within the lumen and side channel, and movable between extended and retracted positions for capturing suture.

8 Claims, 15 Drawing Sheets

(52) U.S. Cl.
CPC .... *A61B 17/06109* (2013.01); *A61B 17/0485* (2013.01); *A61B 2017/00115* (2013.01); *A61B 2017/06009* (2013.01); *A61B 2017/06042* (2013.01)

(58) Field of Classification Search
CPC  A61B 2017/00115; A61B 2017/06009; A61B 17/0485
See application file for complete search history.

(56) References Cited

U.S. PATENT DOCUMENTS

| | | |
|---|---|---|
| 373,372 A | 11/1887 | King |
| 421,919 A | 2/1890 | Fergen |
| 424,518 A | 4/1890 | Van Norman |
| 652,175 A | 6/1900 | Felson |
| 659,422 A | 10/1900 | Shidler |
| 671,337 A | 4/1901 | Gibson |
| 786,000 A | 3/1905 | Botkin |
| 854,147 A | 5/1907 | Carillon |
| 919,138 A | 4/1909 | Drake et al. |
| 1,009,065 A | 11/1911 | Hahn et al. |
| 1,037,864 A | 9/1912 | Carlson et al. |
| 1,066,317 A | 7/1913 | Pirnat |
| 1,293,565 A | 2/1919 | Smit |
| 1,449,087 A | 3/1923 | Bugbee |
| 1,464,832 A | 8/1923 | Richardson |
| 1,579,379 A | 4/1926 | Marbel |
| 1,635,066 A | 7/1927 | Wells |
| 1,641,077 A | 8/1927 | Fouguet |
| 1,656,467 A | 1/1928 | Blake |
| 1,815,725 A | 7/1931 | Pilling et al. |
| 1,822,330 A | 9/1931 | Ainslie |
| 1,855,546 A | 4/1932 | File |
| 1,856,721 A | 5/1932 | Nagelmann |
| 1,876,792 A | 9/1932 | Thompson |
| 1,933,024 A | 10/1933 | Nagelmann |
| 2,023,807 A | 12/1935 | Gruss et al. |
| 2,042,403 A | 5/1936 | Hrivnak |
| 2,065,659 A | 12/1936 | Cullen |
| 2,212,830 A | 9/1940 | Anastasi |
| 2,316,297 A | 4/1943 | Southerland et al. |
| 2,348,218 A | 5/1944 | Karle |
| 2,396,180 A | 7/1944 | Karle |
| 2,414,746 A | 7/1944 | Karle |
| 2,411,118 A | 11/1946 | Schuster |
| 2,414,882 A | 1/1947 | Longfellow |
| 2,434,133 A | 1/1948 | Volk |
| 2,577,240 A | 12/1951 | Findley |
| 2,579,192 A | 12/1951 | Kohl |
| 2,593,622 A | 4/1952 | Stanelle |
| 2,601,564 A | 6/1952 | Smith |
| 2,610,631 A | 9/1952 | Calicchio |
| 2,611,366 A | 9/1952 | Mull |
| 2,646,045 A | 7/1953 | Priestley |
| 2,808,055 A | 10/1957 | Thayer |
| 2,880,728 A | 4/1959 | Rights |
| 2,895,478 A | 7/1959 | Post |
| 2,959,172 A | 11/1960 | Held |
| 3,013,559 A | 12/1961 | Thomas |
| 3,036,482 A | 5/1962 | Kenworthy et al. |
| 3,073,311 A | 1/1963 | Tibbs et al. |
| 3,090,386 A | 5/1963 | Curtis |
| 3,139,089 A | 6/1964 | Schwerin |
| 2,738,790 A | 3/1965 | Todt et al. |
| 3,349,772 A | 10/1967 | Rygg |
| 3,372,477 A | 3/1968 | Hoppe |
| 3,393,687 A | 7/1968 | Whitman |
| 3,417,752 A | 12/1968 | Butler |
| 3,470,834 A | 10/1969 | Bone |
| 3,470,875 A | 10/1969 | Johnson |
| 3,638,653 A | 2/1972 | Berry |
| 3,687,138 A | 8/1972 | Jarvik |
| 3,716,058 A | 2/1973 | Tanner, Jr. |
| 3,752,516 A | 8/1973 | Mumma |
| 3,763,860 A | 10/1973 | Clarke |
| 3,807,407 A | 4/1974 | Schweizer |
| 3,840,017 A | 10/1974 | Violante |
| 3,842,824 A | 10/1974 | Neufeld |
| 3,842,840 A | 10/1974 | Schweizer |
| 3,856,018 A | 12/1974 | Perisse et al. |
| 3,871,379 A | 3/1975 | Clarke |
| 3,890,975 A | 6/1975 | McGregor |
| 3,901,244 A | 8/1975 | Schweizer |
| 3,946,740 A | 3/1976 | Bassett |
| 3,980,177 A | 9/1976 | McGregor |
| 3,985,138 A | 10/1976 | Jarvik |
| 3,990,619 A | 11/1976 | Russell |
| 4,027,608 A | 6/1977 | Arbuckle |
| 4,064,881 A | 12/1977 | Meredith |
| 4,109,658 A | 8/1978 | Hughes |
| 4,161,951 A | 7/1979 | Scanlan, Jr. |
| 4,164,225 A | 8/1979 | Johnson et al. |
| 4,169,476 A | 10/1979 | Hiltebrandt |
| 4,224,947 A | 9/1980 | Fukuda |
| 4,235,238 A | 11/1980 | Ogui et al. |
| 4,236,470 A | 12/1980 | Stenson |
| 4,312,337 A | 1/1982 | Donohue |
| 4,326,531 A | 4/1982 | Shimonaka |
| 4,345,600 A | 8/1982 | Rothfuss |
| 4,345,601 A | 8/1982 | Fukuda |
| 4,373,530 A | 2/1983 | Kilejian |
| 4,384,406 A | 5/1983 | Tischlinger |
| 4,414,466 A | 11/1983 | Fischer et al. |
| 4,414,908 A | 11/1983 | Yasukata |
| 4,423,729 A | 1/1984 | Gray |
| 4,440,171 A | 4/1984 | Nomoto et al. |
| 4,441,497 A | 4/1984 | Paulder |
| 4,448,194 A | 5/1984 | DiGiovanni et al. |
| 4,463,753 A | 8/1984 | Gustilo |
| 4,471,781 A | 9/1984 | Di Giovanni et al. |
| 4,493,323 A | 1/1985 | Albright et al. |
| 4,500,024 A | 2/1985 | DiGiovanni et al. |
| 4,509,516 A | 4/1985 | Richmond |
| 4,512,344 A | 4/1985 | Barber |
| 4,535,768 A | 8/1985 | Hourahane et al. |
| 4,539,474 A | 9/1985 | Takahata |
| 4,553,543 A | 11/1985 | Amarasinghe |
| 4,553,544 A | 11/1985 | Nomoto et al. |
| 4,557,265 A | 12/1985 | Andersson |
| 4,574,805 A | 3/1986 | Lerner |
| 4,580,563 A | 4/1986 | Gross |
| 4,590,929 A | 5/1986 | Klien |
| 4,596,249 A | 6/1986 | Freda et al. |
| 4,602,635 A | 7/1986 | Mulhollan et al. |
| 4,621,639 A | 11/1986 | Transue et al. |
| 4,621,640 A | 11/1986 | Mulhollan et al. |
| 4,633,869 A | 1/1987 | Schmeiding |
| 4,636,121 A | 1/1987 | Miller |
| 4,641,652 A | 2/1987 | Hutter et al. |
| 4,643,178 A | 2/1987 | Nastari et al. |
| 4,660,559 A | 4/1987 | McGregor et al. |
| 4,662,068 A | 5/1987 | Polonsky |
| 4,712,545 A | 12/1987 | Honkanen |
| 4,716,893 A | 1/1988 | Fischer et al. |
| 4,723,546 A | 2/1988 | Zagorski |
| 4,724,840 A | 2/1988 | McVay et al. |
| 4,739,751 A | 4/1988 | Sapega et al. |
| 4,741,330 A | 5/1988 | Hayhurst |
| 4,778,468 A | 10/1988 | Hunt et al. |
| 4,779,616 A | 10/1988 | Johnson |

(56) References Cited

U.S. PATENT DOCUMENTS

| | | |
|---|---|---|
| 4,781,190 A | 11/1988 | Lee |
| 4,787,377 A | 11/1988 | Laboureau |
| 4,790,312 A | 12/1988 | Capuano et al. |
| 4,836,205 A | 6/1989 | Barrett |
| 4,846,799 A | 7/1989 | Tanaka et al. |
| 4,870,957 A | 10/1989 | Globe et al. |
| 4,871,289 A | 10/1989 | Choinere |
| 4,881,537 A | 11/1989 | Henning |
| 4,884,572 A | 12/1989 | Bays et al. |
| 4,890,615 A | 1/1990 | Caspari et al. |
| 4,895,148 A | 1/1990 | Bays et al. |
| 4,899,743 A | 2/1990 | Nicholson et al. |
| 4,915,107 A | 4/1990 | Rebuffat et al. |
| 4,923,461 A | 5/1990 | Caspari et al. |
| 4,926,860 A | 5/1990 | Stice et al. |
| 4,932,961 A | 6/1990 | Wong et al. |
| 4,935,027 A | 6/1990 | Yoon |
| 4,950,285 A | 8/1990 | Wilk |
| 4,957,498 A | 8/1990 | Caspari et al. |
| 4,955,897 A | 9/1990 | Ship |
| 4,961,741 A | 10/1990 | Hayhurst |
| 4,976,715 A | 12/1990 | Bays et al. |
| 5,002,563 A | 3/1991 | Pyka et al. |
| 5,013,292 A | 5/1991 | Lemay |
| 5,015,250 A | 5/1991 | Foster |
| 5,026,350 A | 6/1991 | Tanaka et al. |
| 5,037,422 A | 8/1991 | Hayhurst et al. |
| 5,037,433 A | 8/1991 | Wilk et al. |
| 5,053,047 A | 10/1991 | Yoon |
| 5,059,201 A | 10/1991 | Asnis |
| 5,084,058 A | 1/1992 | Li |
| 5,085,661 A | 2/1992 | Moss |
| 5,087,263 A | 2/1992 | Li |
| 5,100,415 A | 3/1992 | Hayhurst |
| 5,100,418 A | 3/1992 | Yoon et al. |
| 5,100,421 A | 3/1992 | Christoudias |
| 5,120,318 A | 6/1992 | Nallapareddy |
| 5,123,913 A | 6/1992 | Wilk et al. |
| 5,129,912 A | 7/1992 | Noda et al. |
| 5,133,723 A | 7/1992 | Li et al. |
| 5,149,329 A | 9/1992 | Richardson |
| 5,152,764 A | 10/1992 | Goble |
| 5,152,769 A | 10/1992 | Baber |
| 5,152,790 A | 10/1992 | Rosenberg et al. |
| 5,163,946 A | 11/1992 | Li |
| 5,174,087 A | 12/1992 | Bruno |
| 5,176,691 A | 1/1993 | Pierce |
| 5,178,629 A | 1/1993 | Kammerer |
| 5,181,919 A | 1/1993 | Bergman et al. |
| 5,188,636 A | 2/1993 | Fedotov |
| 5,192,287 A | 3/1993 | Fournier et al. |
| 5,201,741 A | 4/1993 | Dulebohn |
| 5,201,743 A | 4/1993 | Haber et al. |
| 5,201,744 A | 4/1993 | Jones |
| 5,211,650 A | 5/1993 | Noda |
| 5,217,471 A | 6/1993 | Burkhart |
| 5,217,486 A | 6/1993 | Rice et al. |
| 5,219,358 A | 6/1993 | Bendel et al. |
| 5,222,508 A | 6/1993 | Contarini |
| 5,222,962 A | 6/1993 | Burkhart |
| 5,222,976 A | 6/1993 | Yoon et al. |
| 5,222,977 A | 6/1993 | Esser |
| 5,224,955 A | 7/1993 | West |
| 5,234,443 A | 8/1993 | Phan et al. |
| 5,234,444 A | 8/1993 | Christoudias |
| 5,242,458 A | 9/1993 | Bendel et al. |
| 5,248,231 A | 9/1993 | Denham et al. |
| 5,250,054 A | 10/1993 | Li |
| 5,250,055 A | 10/1993 | Moore et al. |
| 5,254,126 A | 10/1993 | Filipi et al. |
| 5,257,637 A | 11/1993 | El Gazayerli |
| 5,259,846 A | 11/1993 | Granger et al. |
| 5,261,917 A | 11/1993 | Hasson et al. |
| 5,266,075 A | 11/1993 | Clark et al. |
| 5,269,783 A | 12/1993 | Sander |
| 5,269,786 A | 12/1993 | Morgan |
| 5,269,791 A | 12/1993 | Mayzels et al. |
| 5,273,024 A | 12/1993 | Menon et al. |
| 5,275,613 A | 1/1994 | Haber et al. |
| 5,281,234 A | 1/1994 | Wilk et al. |
| 5,282,809 A | 2/1994 | Kammerer et al. |
| 5,292,327 A | 3/1994 | Dodd et al. |
| 5,304,184 A | 4/1994 | Hathaway et al. |
| 5,304,185 A | 4/1994 | Taylor |
| 5,306,280 A | 4/1994 | Bregan et al. |
| 5,308,353 A | 5/1994 | Feurrier |
| 5,312,422 A | 5/1994 | Trott |
| 5,368,601 A | 5/1994 | Beurrier |
| 5,318,577 A | 6/1994 | Li |
| 5,318,579 A | 6/1994 | Chow |
| 5,320,632 A | 6/1994 | Heidmueller |
| 5,327,896 A | 7/1994 | Schmieding |
| 5,334,198 A | 8/1994 | Hart et al. |
| 5,336,239 A | 8/1994 | Gimpelson |
| 5,356,419 A | 10/1994 | Chow |
| 5,364,408 A | 11/1994 | Gordon |
| 5,364,409 A | 11/1994 | Kuwabara et al. |
| 5,368,606 A | 11/1994 | Marlow et al. |
| 5,372,604 A | 12/1994 | Trott |
| 5,374,275 A | 12/1994 | Bradley |
| 5,376,096 A | 12/1994 | Foster |
| 5,382,257 A | 1/1995 | Lewis et al. |
| 5,387,221 A | 2/1995 | Bisgaard |
| 5,387,227 A | 2/1995 | Grice |
| 5,389,103 A | 2/1995 | Melzer et al. |
| 5,391,170 A | 2/1995 | McGuire et al. |
| 5,391,173 A | 2/1995 | Wilk |
| 5,393,302 A | 2/1995 | Clark et al. |
| 5,397,325 A | 3/1995 | Della Badia et al. |
| 5,403,328 A | 4/1995 | Shallman |
| 5,403,329 A | 4/1995 | Hinchcliffe |
| 5,409,494 A | 4/1995 | Morgan |
| 5,417,699 A | 5/1995 | Klein et al. |
| 5,417,701 A | 5/1995 | Holmes |
| 5,423,837 A | 6/1995 | Mericle et al. |
| 5,425,733 A | 6/1995 | Schmieding |
| 5,431,678 A | 7/1995 | Rogers |
| 5,433,722 A | 7/1995 | Sharpe et al. |
| 5,439,467 A | 8/1995 | Benderev et al. |
| 5,441,502 A | 8/1995 | Bartlett |
| 5,441,507 A | 8/1995 | Wilk |
| 5,443,509 A | 8/1995 | Boucher et al. |
| 5,449,367 A | 9/1995 | Kadry |
| 5,454,823 A | 10/1995 | Richardson et al. |
| 5,456,246 A | 10/1995 | Schmieding et al. |
| 5,462,562 A | 10/1995 | Elkus |
| 5,464,425 A | 11/1995 | Skiba |
| 5,466,243 A | 11/1995 | Schmieding et al. |
| 5,470,338 A | 11/1995 | Whitfield et al. |
| 5,474,565 A | 12/1995 | Trott |
| 5,478,344 A | 12/1995 | Stone et al. |
| 5,478,345 A | 12/1995 | Stone et al. |
| 5,480,406 A | 1/1996 | Nolan et al. |
| 5,496,331 A | 3/1996 | Xu et al. |
| 5,496,335 A | 3/1996 | Thomason et al. |
| 5,499,991 A | 3/1996 | Garman et al. |
| 5,501,688 A | 3/1996 | Whiteside et al. |
| 5,501,692 A | 3/1996 | Riza |
| D368,776 S | 4/1996 | Toy et al. |
| 5,505,735 A | 4/1996 | Li |
| 5,507,755 A | 4/1996 | Gresl et al. |
| 5,507,757 A | 4/1996 | Sauer et al. |
| 5,520,696 A | 5/1996 | Wenstrom, Jr. |
| 5,520,703 A | 5/1996 | Essig et al. |
| 5,522,820 A | 6/1996 | Caspari et al. |
| 5,527,321 A | 6/1996 | Hinchliffe |
| 5,527,322 A | 6/1996 | Klien et al. |
| 5,540,705 A | 7/1996 | Meade et al. |
| 5,545,170 A | 8/1996 | Hart |
| 5,549,613 A | 8/1996 | Goble et al. |
| 5,549,618 A | 8/1996 | Fleenor et al. |
| 5,549,636 A | 8/1996 | Li |
| 5,554,171 A | 9/1996 | Gattuma et al. |
| 5,562,683 A | 10/1996 | Chan |

(56) References Cited

U.S. PATENT DOCUMENTS

| | | |
|---|---|---|
| 5,562,686 A | 10/1996 | Sauer et al. |
| 5,562,687 A | 10/1996 | Chan |
| 5,562,696 A | 10/1996 | Nobles et al. |
| 5,565,122 A | 10/1996 | Zinnbauer et al. |
| 5,569,269 A | 10/1996 | Hart et al. |
| 5,569,299 A | 10/1996 | Dill et al. |
| 5,569,301 A | 10/1996 | Granger et al. |
| 5,571,090 A | 11/1996 | Sherts |
| 5,573,008 A | 11/1996 | Robinson |
| 5,573,542 A | 11/1996 | Stevens |
| 5,573,543 A | 11/1996 | Stevens |
| 5,575,801 A | 11/1996 | Habermeyer et al. |
| 5,578,044 A | 11/1996 | Gordon et al. |
| 5,584,835 A | 12/1996 | Greenfield |
| 5,586,986 A | 12/1996 | Hinchiffe |
| 5,591,179 A | 1/1997 | Edelstein |
| 5,591,180 A | 1/1997 | Hinchliffe |
| 5,601,557 A | 2/1997 | Hayhurst |
| 5,601,571 A | 2/1997 | Moss |
| 5,603,718 A | 2/1997 | Xu |
| 5,607,435 A | 3/1997 | Sachdeva et al. |
| 5,618,290 A | 4/1997 | Toy et al. |
| 5,618,304 A | 4/1997 | Hart et al. |
| 5,626,588 A | 5/1997 | Sauer et al. |
| 5,626,590 A | 5/1997 | Wilk |
| 5,630,825 A | 5/1997 | de la Torre et al. |
| 5,632,748 A | 5/1997 | Beck, Jr. et al. |
| 5,632,751 A | 5/1997 | Piraka |
| 5,643,266 A | 7/1997 | Li |
| 5,643,289 A | 7/1997 | Sauer et al. |
| 5,643,292 A | 7/1997 | Hart |
| 5,645,552 A | 7/1997 | Sheds |
| 5,649,939 A | 7/1997 | Reddick |
| 5,653,716 A | 8/1997 | Malo et al. |
| 5,658,289 A | 8/1997 | Boucher et al. |
| 5,658,299 A | 8/1997 | Hart |
| 5,662,658 A | 9/1997 | Wenstrom, Jr. |
| 5,662,665 A | 9/1997 | Ludwick |
| 5,665,096 A | 9/1997 | Yoon |
| 5,667,526 A | 9/1997 | Levin |
| 5,674,229 A | 10/1997 | Tovey et al. |
| 5,674,230 A | 10/1997 | Tovey et al. |
| 5,681,333 A | 10/1997 | Burkhart et al. |
| 5,690,652 A | 11/1997 | Wurster et al. |
| 5,690,653 A | 11/1997 | Richardson et al. |
| 5,690,677 A | 11/1997 | Schmieding et al. |
| 5,693,061 A | 12/1997 | Pierce et al. |
| 5,693,071 A | 12/1997 | Gorecki et al. |
| 5,695,522 A | 12/1997 | LeMaire, III et al. |
| 5,697,950 A | 12/1997 | Fucci et al. |
| 5,700,023 A | 12/1997 | Buelna et al. |
| 5,700,273 A | 12/1997 | Buelna et al. |
| 5,707,379 A | 1/1998 | Fleenor et al. |
| 5,709,694 A | 1/1998 | Greenberg et al. |
| 5,713,908 A | 2/1998 | Jameel et al. |
| 5,728,107 A | 3/1998 | Zlock et al. |
| 5,728,112 A | 3/1998 | Yoon |
| 5,728,113 A | 3/1998 | Sherts |
| 5,728,135 A | 3/1998 | Bregen et al. |
| 5,730,747 A | 3/1998 | Ek et al. |
| 5,735,862 A | 4/1998 | Jennings et al. |
| 5,741,278 A | 4/1998 | Stevens |
| 5,746,751 A | 5/1998 | Sherts |
| 5,746,753 A | 5/1998 | Sullivan et al. |
| 5,749,879 A | 5/1998 | Middleman et al. |
| 5,752,964 A | 5/1998 | Mericle |
| 5,755,728 A | 5/1998 | Maki |
| 5,759,188 A | 6/1998 | Yoon |
| 5,772,672 A | 6/1998 | Toy et al. |
| 5,792,152 A | 8/1998 | Klein et al. |
| 5,797,927 A | 8/1998 | Yoon |
| 5,800,447 A | 9/1998 | Wenstrom, Jr. |
| 5,810,848 A | 9/1998 | Hayhurst |
| 5,810,852 A | 9/1998 | Greenberg et al. |
| 5,814,052 A | 9/1998 | Nakao et al. |
| 5,814,054 A | 9/1998 | Kortenbach et al. |
| 5,814,069 A | 9/1998 | Schulze et al. |
| 5,817,107 A | 10/1998 | Schaller |
| 5,817,111 A | 10/1998 | Riza |
| 5,826,776 A | 10/1998 | Schulze et al. |
| 5,827,298 A | 10/1998 | Hart et al. |
| 5,827,299 A | 10/1998 | Thomason et al. |
| 5,830,220 A | 11/1998 | Wan et al. |
| 5,833,697 A | 11/1998 | Ludwick |
| 5,843,084 A | 12/1998 | Hart et al. |
| 5,843,099 A | 12/1998 | Nichols et al. |
| 5,843,100 A | 12/1998 | Meade |
| 5,846,254 A | 12/1998 | Schulze et al. |
| 5,855,311 A | 1/1999 | Hamblin et al. |
| 5,860,749 A | 1/1999 | Hirakawa et al. |
| 5,860,983 A | 1/1999 | Wenstrom, Jr. |
| 5,860,992 A | 1/1999 | Daniel et al. |
| 5,865,835 A | 2/1999 | Lolagne |
| 5,871,488 A | 2/1999 | Tovey et al. |
| 5,871,490 A | 2/1999 | Schulze et al. |
| 5,876,412 A | 3/1999 | Piraka |
| 5,879,371 A | 3/1999 | Gardomer et al. |
| 5,893,878 A | 4/1999 | Pierce |
| 5,895,393 A | 4/1999 | Pagedas |
| 5,895,395 A | 4/1999 | Yeung |
| 5,897,563 A | 4/1999 | Yoon et al. |
| 5,897,564 A | 4/1999 | Shultz et al. |
| 5,897,574 A | 4/1999 | Bonutti |
| 5,899,911 A | 5/1999 | Carter |
| 5,904,692 A | 5/1999 | Steckel et al. |
| 5,908,426 A | 6/1999 | Pierce |
| 5,908,428 A | 6/1999 | Scirica et al. |
| 5,910,148 A | 6/1999 | Reimels et al. |
| 5,918,604 A | 7/1999 | Whelan |
| 5,919,199 A | 7/1999 | Mers Kelly et al. |
| 5,925,064 A | 7/1999 | Meyers et al. |
| 5,928,252 A | 7/1999 | Steadman et al. |
| 5,931,844 A | 8/1999 | Thompson et al. |
| 5,935,149 A | 8/1999 | Ek |
| 5,938,668 A | 8/1999 | Scirica et al. |
| 5,941,439 A | 8/1999 | Kammerer et al. |
| 5,944,724 A | 8/1999 | Lizardi |
| 5,947,982 A | 9/1999 | Duran |
| 5,951,559 A | 9/1999 | Burkhart |
| 5,951,587 A | 9/1999 | Qureshi et al. |
| 5,954,733 A | 9/1999 | Yoon |
| 5,957,937 A | 9/1999 | Yoon |
| 5,964,773 A | 10/1999 | Greenstein |
| 5,968,047 A | 10/1999 | Reed |
| 5,980,538 A | 11/1999 | Fuchs et al. |
| 5,980,557 A | 11/1999 | Iserin et al. |
| 5,984,932 A | 11/1999 | Yoon |
| 5,993,451 A | 11/1999 | Burkhart |
| 5,993,466 A | 11/1999 | Yoon |
| 5,993,467 A | 11/1999 | Yoon |
| 6,004,332 A | 12/1999 | Yoon et al. |
| 6,010,513 A | 1/2000 | Tomalla et al. |
| 6,017,358 A | 1/2000 | Yoon et al. |
| 6,024,747 A | 2/2000 | Kontos |
| 6,045,561 A | 4/2000 | Marshall et al. |
| 6,051,006 A | 4/2000 | Shluzas et al. |
| 6,071,289 A | 6/2000 | Stefanchik et al. |
| 6,074,403 A | 6/2000 | Nord |
| 6,077,276 A | 6/2000 | Kontos |
| 6,080,180 A | 6/2000 | Yoon et al. |
| 6,086,601 A | 7/2000 | Yoon |
| 6,096,060 A | 8/2000 | Fitts et al. |
| 6,099,538 A | 8/2000 | Moses et al. |
| 6,102,920 A | 8/2000 | Sullivan et al. |
| 6,117,114 A | 9/2000 | Nobles et al. |
| 6,117,144 A | 9/2000 | Nobles |
| 6,126,665 A | 10/2000 | Yoon |
| 6,132,433 A | 10/2000 | Whelan |
| 6,143,004 A | 11/2000 | Davis et al. |
| 6,143,005 A | 11/2000 | Yoon et al. |
| 6,146,387 A | 11/2000 | Trott et al. |
| 6,146,391 A | 11/2000 | Cigaina |
| 6,159,224 A | 12/2000 | Yoon |
| 6,183,485 B1 | 2/2001 | Thomason et al. |

(56) References Cited

U.S. PATENT DOCUMENTS

| | | |
|---|---|---|
| 6,197,035 B1 | 3/2001 | Loubens et al. |
| 6,200,329 B1 | 3/2001 | Fung et al. |
| 6,254,620 B1 | 7/2001 | Koh et al. |
| 6,322,570 B1 | 11/2001 | Matsutani et al. |
| 6,332,889 B1 | 12/2001 | Sancoff et al. |
| 6,383,199 B2 | 5/2002 | Carter et al. |
| 6,454,777 B1 | 9/2002 | Green |
| 6,461,366 B1 | 10/2002 | Seguin |
| 6,475,135 B1 | 11/2002 | Levy |
| 6,485,504 B1 | 11/2002 | Johnson et al. |
| 6,511,487 B1 | 1/2003 | Oren et al. |
| 6,517,552 B1 | 2/2003 | Nord et al. |
| 6,533,795 B1 | 3/2003 | Tran et al. |
| 6,551,330 B1 | 4/2003 | Bain et al. |
| 6,595,911 B2 | 7/2003 | LoVuolo |
| 6,599,298 B1 | 7/2003 | Forster et al. |
| 6,599,309 B1 | 7/2003 | Gilman |
| 6,605,096 B1 | 8/2003 | Ritchart |
| 6,616,674 B2 | 9/2003 | Schmieding |
| 6,623,492 B1 | 9/2003 | Berube et al. |
| 6,638,283 B2 | 10/2003 | Thal |
| 6,679,895 B1 | 1/2004 | Sancoff et al. |
| 6,719,764 B1 | 4/2004 | Gellman et al. |
| 6,723,107 B1 | 4/2004 | Skiba et al. |
| 6,743,241 B2 | 6/2004 | Kerr |
| 6,770,084 B1 | 8/2004 | Bain et al. |
| 6,843,796 B2 | 1/2005 | Harari et al. |
| 6,896,686 B2 | 5/2005 | Weber |
| 6,984,237 B2 | 1/2006 | Hatch et al. |
| D523,554 S | 6/2006 | Weisel |
| D529,173 S | 9/2006 | Weisel |
| D530,421 S | 10/2006 | Topper et al. |
| 7,585,305 B2 | 9/2009 | Dreyfuss |
| 8,591,527 B2 | 11/2013 | Fan et al. |
| 2002/0055758 A1 | 5/2002 | Sasaki |
| 2002/0065526 A1 | 5/2002 | Oren et al. |
| 2002/0103493 A1 | 8/2002 | Thal |
| 2002/0103494 A1 | 8/2002 | Pacey |
| 2002/0111534 A1 | 8/2002 | Suzuki et al. |
| 2002/0126845 A1 | 9/2002 | Hue et al. |
| 2002/0128666 A1 | 9/2002 | Sancoff et al. |
| 2002/0138084 A1 | 9/2002 | Weber |
| 2002/0147456 A1 | 10/2002 | Diduch et al. |
| 2002/0156344 A1 | 10/2002 | Pasricha et al. |
| 2002/0173800 A1 | 11/2002 | Dreyfuss et al. |
| 2002/0193811 A1 | 12/2002 | Chan |
| 2003/0009186 A1 | 1/2003 | Mastri et al. |
| 2003/0023250 A1 | 1/2003 | Watschke et al. |
| 2003/0065337 A1 | 4/2003 | Topper et al. |
| 2003/0078585 A1 | 4/2003 | Johnson et al. |
| 2003/0078599 A1 | 4/2003 | O'Quinn et al. |
| 2003/0078600 A1 | 4/2003 | O'Quinn et al. |
| 2003/0083695 A1 | 5/2003 | Morris et al. |
| 2003/0105474 A1 | 6/2003 | Bonutti |
| 2003/0144674 A1 | 7/2003 | Loubens et al. |
| 2003/0176874 A1 | 9/2003 | Sauer |
| 2003/0216756 A1 | 11/2003 | Klein et al. |
| 2003/0233108 A1 | 12/2003 | Gellman et al. |
| 2004/0010273 A1 | 1/2004 | Diduch et al. |
| 2004/0073254 A1 | 4/2004 | Wyman et al. |
| 2004/0127915 A1 | 7/2004 | Fleenor et al. |
| 2004/0193185 A1 | 9/2004 | McBrayer |
| 2004/0199184 A1 | 10/2004 | Topper et al. |
| 2004/0249393 A1 | 12/2004 | Weisel et al. |
| 2004/0249394 A1 | 12/2004 | Morris et al. |
| 2004/0260314 A1 | 12/2004 | Lizardi et al. |
| 2005/0021052 A1 | 1/2005 | Kim |
| 2005/0043748 A1 | 2/2005 | Oren et al. |
| 2005/0240219 A1 | 10/2005 | Kahle et al. |
| 2005/0251178 A1 | 11/2005 | Tirabassi et al. |
| 2006/0036265 A1 | 2/2006 | Dant et al. |
| 2006/0069399 A1 | 3/2006 | Weisel et al. |
| 2007/0010829 A1 | 1/2007 | Nobles et al. |
| 2007/0016249 A1 | 1/2007 | Reznik |
| 2007/0038230 A1 | 2/2007 | Stone et al. |
| 2007/0118152 A1 | 5/2007 | Page |
| 2007/0156172 A1 | 7/2007 | Alvarado |
| 2008/0027468 A1 | 1/2008 | Fenton et al. |
| 2008/0114378 A1 | 5/2008 | Matsushita |
| 2008/0154286 A1 | 6/2008 | Abbott et al. |
| 2008/0234729 A1 | 9/2008 | Page et al. |
| 2008/0255591 A1 | 10/2008 | Harada et al. |
| 2009/0018554 A1 | 1/2009 | Thorne et al. |
| 2009/0062819 A1 | 3/2009 | Burkhart et al. |
| 2009/0069824 A1 | 3/2009 | Chu |
| 2009/0069845 A1 | 3/2009 | Frushell et al. |
| 2009/0082787 A1 | 3/2009 | Pang |
| 2009/0082788 A1 | 3/2009 | Elmaraghy |
| 2009/0131956 A1 | 5/2009 | Dewey et al. |
| 2009/0131976 A1 | 5/2009 | Kowalski |
| 2009/0198274 A1 | 8/2009 | Frushell et al. |
| 2010/0042117 A1 | 2/2010 | Kim et al. |
| 2010/0076440 A1 | 3/2010 | Pamichev et al. |
| 2010/0198235 A1 | 8/2010 | Pierce et al. |
| 2010/0268241 A1 | 10/2010 | Flom et al. |
| 2010/0312179 A1 | 12/2010 | Nikolchev et al. |
| 2011/0087247 A1 | 4/2011 | Fung et al. |
| 2011/0245850 A1 | 10/2011 | van der Burg et al. |
| 2012/0123448 A1* | 5/2012 | Flom ............ A61B 17/0469 606/144 |
| 2012/0209300 A1 | 8/2012 | Torrie |
| 2013/0035699 A1 | 2/2013 | Heneveld et al. |
| 2013/0046336 A1 | 2/2013 | Blumenkranz |
| 2014/0188138 A1 | 7/2014 | Melsheimer |
| 2014/0222033 A1* | 8/2014 | Foerster ............ A61B 17/0469 606/144 |

FOREIGN PATENT DOCUMENTS

| | | |
|---|---|---|
| DE | 321755 C | 6/1920 |
| DE | 9109097 U1 | 9/1991 |
| DE | 9112301 U1 | 11/1991 |
| DE | 9203041 U1 | 5/1992 |
| DE | 1235602 A1 | 4/1994 |
| EP | 0136262 A2 | 4/1985 |
| EP | 0207545 A1 | 1/1987 |
| EP | 0315371 A2 | 5/1989 |
| EP | 0903109 A1 | 3/1990 |
| EP | 0535906 A2 | 4/1993 |
| EP | 0574707 A1 | 12/1993 |
| EP | 0668056 A1 | 8/1995 |
| EP | 0684012 A2 | 11/1995 |
| EP | 0717957 A1 | 6/1996 |
| EP | 0778004 A1 | 6/1997 |
| EP | 0792621 A1 | 9/1997 |
| EP | 1243221 A2 | 9/2002 |
| EP | 1334697 A1 | 8/2003 |
| EP | 2353516 A1 | 8/2011 |
| GB | 630693 A | 10/1949 |
| GB | 2260704 A | 4/1993 |
| JP | 10542161 A | 2/1993 |
| JP | H07250839 A | 10/1995 |
| JP | H08215200 A | 8/1996 |
| JP | 2002336263 A | 11/2002 |
| JP | 2007050200 A | 3/2007 |
| JP | 2008538510 A | 10/2008 |
| SU | 552077 A1 | 3/1977 |
| WO | 1989010096 A1 | 11/1989 |
| WO | 1992012674 A1 | 8/1992 |
| WO | 1994028801 A1 | 12/1994 |
| WO | 1995002363 A1 | 1/1995 |
| WO | 1995008958 A1 | 4/1995 |
| WO | 1995013021 A1 | 5/1995 |
| WO | 1996009796 A2 | 4/1996 |
| WO | 1996027331 A1 | 9/1996 |
| WO | 1996039946 A1 | 12/1996 |
| WO | 1996039948 A1 | 12/1996 |
| WO | 1997041780 A1 | 11/1997 |
| WO | 1997047246 A1 | 12/1997 |
| WO | 1998014126 A1 | 4/1998 |
| WO | 1998030151 A1 | 7/1998 |
| WO | 1998030152 A1 | 7/1998 |
| WO | 1998030153 A1 | 7/1998 |
| WO | 1998043545 A1 | 10/1998 |

(56) References Cited

FOREIGN PATENT DOCUMENTS

| WO | 1999012480 A1 | 3/1999 |
| WO | 1999047050 A2 | 9/1999 |
| WO | 2000012013 A1 | 3/2000 |
| WO | 2000051498 A1 | 9/2000 |
| WO | 2001078609 A2 | 10/2001 |
| WO | 2001095809 A1 | 12/2001 |
| WO | 2002004322 A2 | 1/2002 |
| WO | 2002043558 A2 | 6/2002 |
| WO | 2003099136 A1 | 12/2003 |
| WO | 2006023975 A2 | 3/2006 |
| WO | 2009138103 A1 | 11/2009 |
| WO | 2011008607 A1 | 1/2011 |
| WO | 2013119592 A1 | 8/2013 |

OTHER PUBLICATIONS

Lore, J.M., Tender Grip Forceps, American Journal of Surgery, vol. 104, Jul. 1962.
1997 Products Catalog, Smith & Nephew Inc., Shoulder Arthroscopy, 3 pages, Printed Mar. 1997.
1998 Products Catalog, Endoscopy Division, Smith & Nephew, Inc., Shoulder Arthroscopy, 6 pages, Mar. 1998.
1999 Products Catalog, Endoscopy Division, Smith & Nephew, Inc., Shoulder Arthroscopy, 3 pages, Mar. 1999.
2001 Products Catalog U.S. Market, Endoscopy Division, Smith & Nephew, Inc., Shoulder Arthroscopy, 3 pages, Dec. 2000.
2002 Products Catalog U.S. Market, Endoscopy Division, Smith & Nephew, Inc., Knee Arthroscopy, 6 pages, Printed Dec. 2001.
Elite and Arthro-Pierce Shoulder Instrument Systems Brochure, 2001, Smith & Nephew, Inc., 4 page, printed Feb. 2001.
Introducting the Acufex Suture Punch Suturing made simple. 1997, Smith & Nephew, Inc., 1 page.
Esch, J., Arthroscopic Rotator Cuff Repair with the Elite Shoulder System, A Smith & Nephew Technique Plus Illustrated Guide, 2001, Smith & Nephew, Inc., 15 page, Oct. 2001.
Closing the Gap in Soft Tissue Repair, The AutoCuff System, 2003, Opus Medical, Inc., 4 pages.
The Elite Shoulder System Brochure, 1999, OBL, Inc., 4 pages.
Golano, P. et al., Arthroscopic Anatomy of Posterior Ankle Ligaments, Arthroscopy: The Journal of Arthroscopic and Related Surgery, vol. 18, No. 4 (Apr. 2002): pp. 353-358.
The Easy-to-us ArthroSew Suturing System for passing braided suture fast and effectively, 1997, Surgical Dynamics, 2 pages, May 1997.
Acufex Suture Punch Suturing made simple. 1997, Smith & Nephew, Inc., 2 pages, Feb. 1997.
Field, L.D., The Elite Arthroscopic Rotator Cuff Repair Shoulder System, 1999, OBL, Inc., 4 pages.
Arthrex Transtibial PCL Reconstruction Surgical Technique Manual, 29 pages.
Arthrex, FASTak and Corkscrew Suture Anchor System for Rotator Cuff Repair, 1996 Smith & Nephew, Inc., 1 page.
Elite and Arhtro-Pierce Shoulder Instrument Systems Ordering Information, 2002, Smith & Nephew, Inc., 2 pages, Aug. 2002.
Esch, J., The Elite Arthroscopic Rotator Cuff Repair Shoulder System, 1999, OBL, Inc., 12 pages.
OBL Arthro-Pierce Making It Simple, 2000, OBL, Inc., 2 pages.
Field, L.D., The Elite Shoulder System, 1999, OBL, Inc., 4 pages.
OBL, Hospital Price List, Jul. 1, 2000, OBL, Inc., 4 pages.
From our skilled hands to yours. Hand-Held Instrument Guide, 1997, Smith & Nephew, Inc., 13 pages, Aug. 18, 1997.
The Complete System for Shoulder Arthroscopy, Innovative Solutions for Arthroscopists, 2000, T.A.G. Medical Products, 7 pages, Jan. 2001 and Feb. 2000.
Arthrex Transtibial Arthroscopic PCL Reconstruction Surgical Technique Manual, 1999, Arthrex, Inc., 27 pages.
Arthrex Transtibial Single Incision ACL Reconstruction using Three Autograft Options, 1998, Arthrex, Inc., 32 pages.
Suture Punch, 1993, ArthroTek, Inc., 2 pages.
The ExpressSew, Suture Passer, The 5mm Solution for Tissue Repair, 2002, Surgical Solutions, LLC, 5 pages.
Introducing the Acufex Suture Punch, 1997, Smith & Nephew, Inc., 4 pages, Jan. 1997.
ExpressSew, Suture Passer, Surgical Solutions, 5 pages, Apr. 2003.
Romeo, A. A., Arthroscopic Repair of Full-Thickness Rotator Cuff Tears: Surgical Technique and Instrumentation, Orthopedic Special Edition, vol. 7, No. 1 of 2, 2001, pp. 25-28.
Morgan, C.D. et al. "Arthoroscopic Meniscus Repair: A Safe Approach to the Posterior Horns", Arthroscopy: The Journal of Arthroscopic of Related Surgery, vol. 2, No. 1, 1986 (10 pages).
International Preliminary Report on Patentability from related PCT Application No. PCT/US15/027640 dated Oct. 25, 2016.

\* cited by examiner

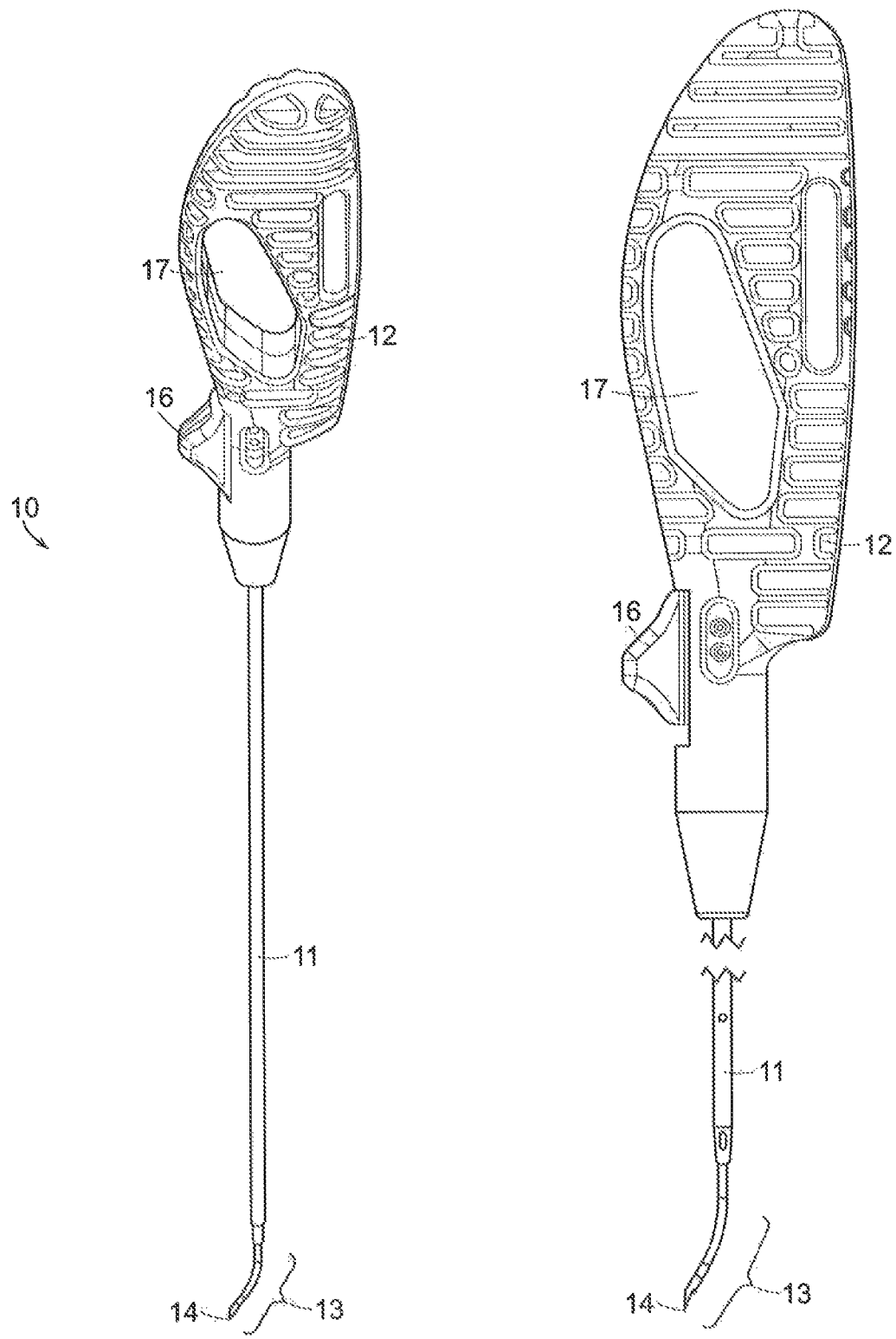

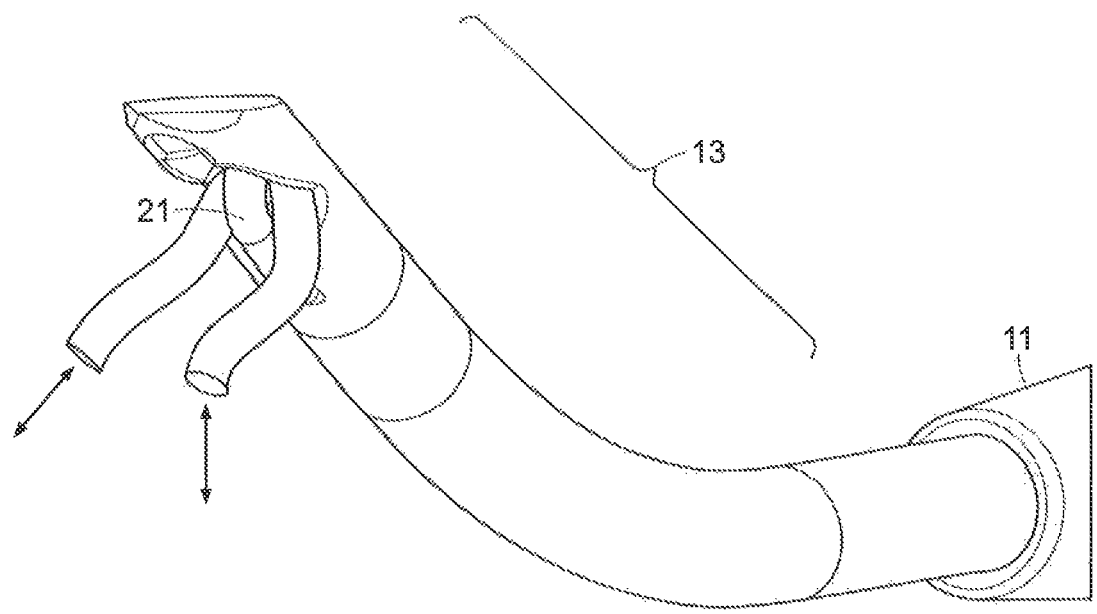
FIG. 4
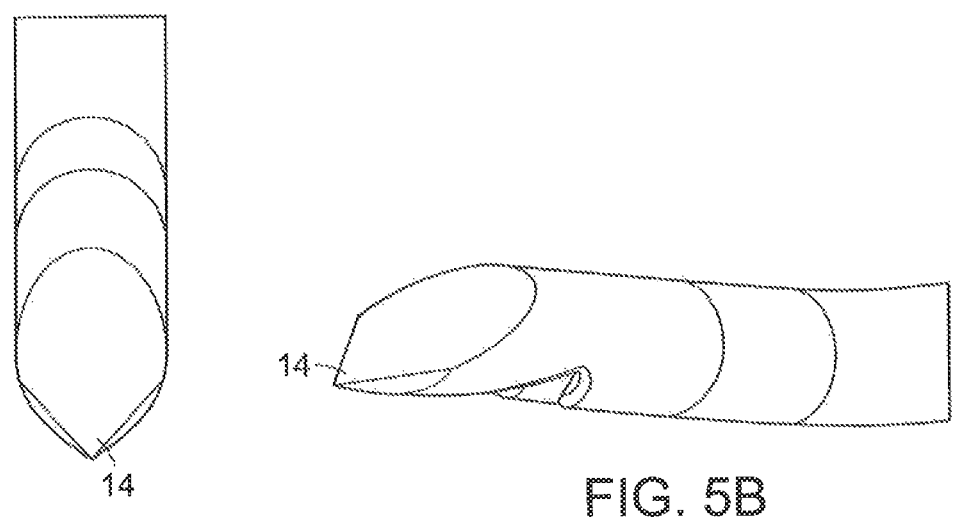
FIG. 5A
FIG. 5B

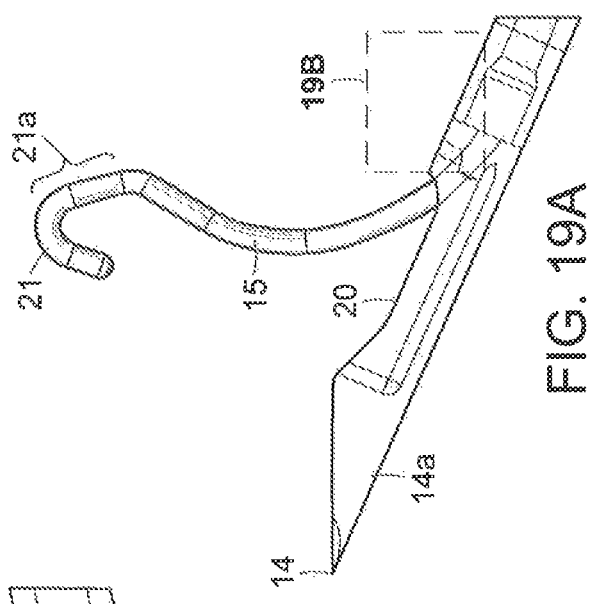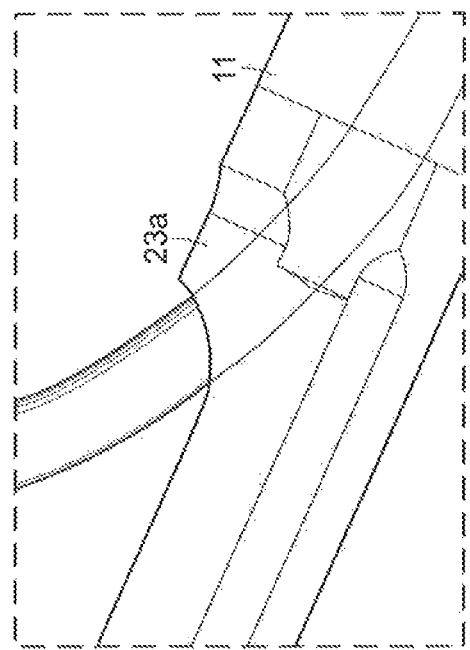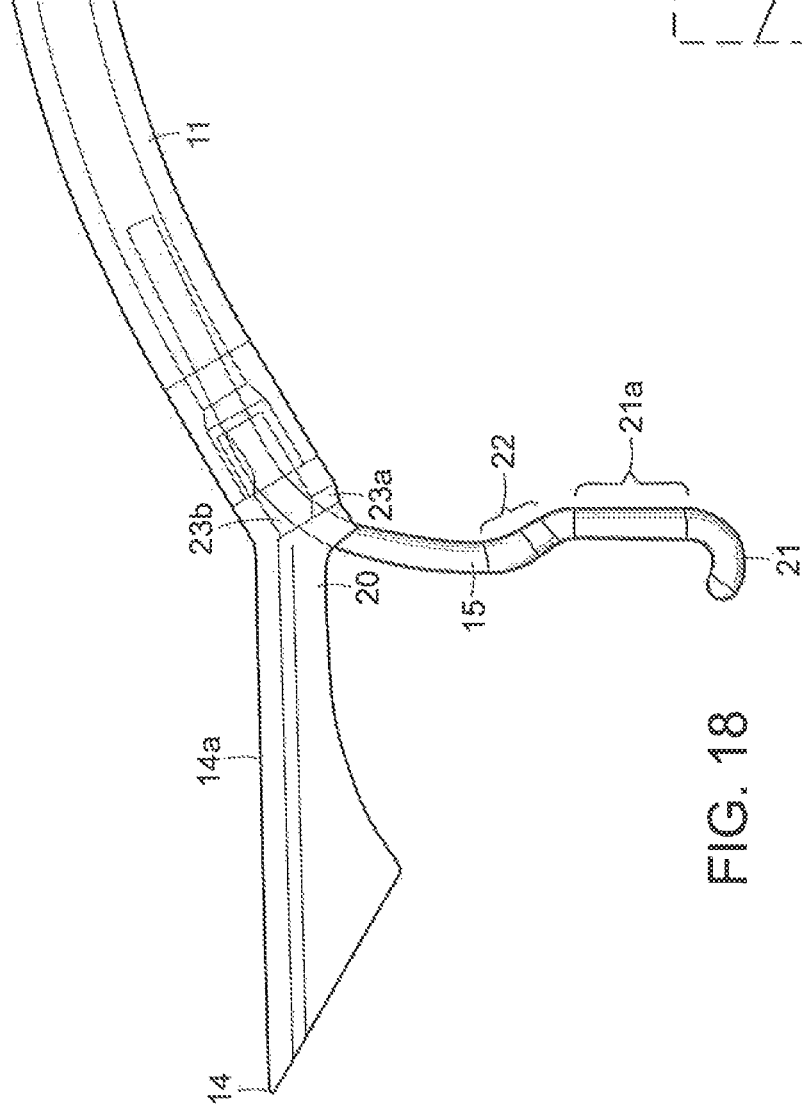

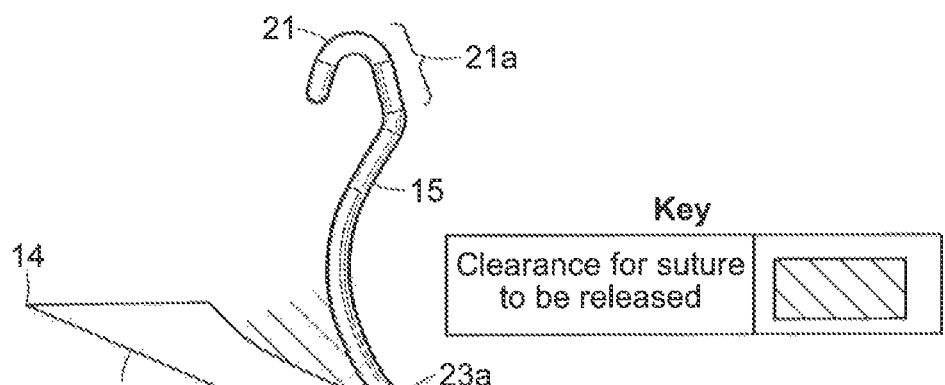
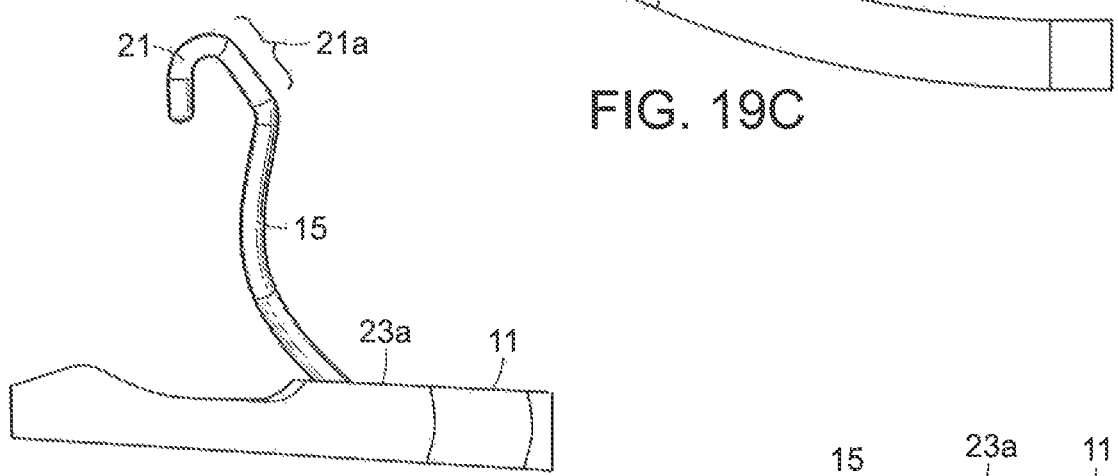
FIG. 19C
FIG. 20A
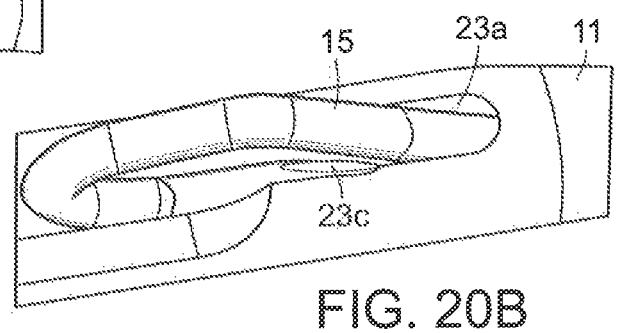
FIG. 20B
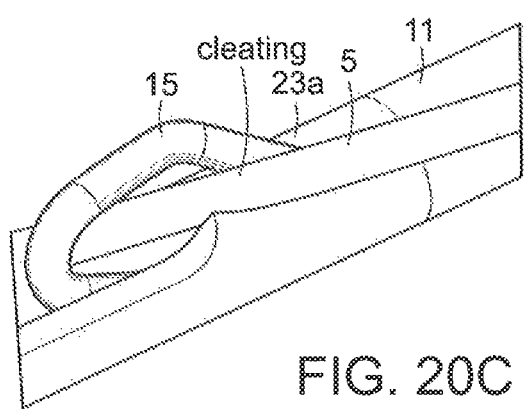
FIG. 20C

SUTURE PASSER

CROSS-REFERENCE TO RELATED APPLICATIONS

This application claims the benefit of and is a national stage entry of PCT/US15/27640, filed Apr. 24, 2015 which, in turn, claims the benefit of U.S. Provisional Application No. 61/983,487, filed Apr. 24, 2014, the disclosure of which is incorporated by reference herein in its entirety.

This application also relates to but does not claim priority to U.S. Patent Publication No. 2014/0222033 to Seath A. Foerster, et al., the disclosure of which is incorporated by reference herein in its entirety.

BACKGROUND

The present disclosure concerns a surgical instrument for manipulating suture. In particular, the present disclosure relates to an instrument for passing suture through tissue.

In many surgical procedures, suture is used to close wounds and may be used to repair damage to ligaments and soft tissue. As part of the repair, suture may be routed through tissues to stitch or hold the tissue together, or for the purposes of capturing the tissue and anchoring it to a surgical implant such as a suture anchor. Known instruments for suture passing typically consist of a piercing portion or needle, which may be curved, and a means for retaining the suture within a portion of the needle to enable the suture to be manipulated and passed through tissue during the repair procedure.

In examples where the suture passing needle is hollow, potential problems may arise through tissue entrapment, where the most distal end of the needle opening may snag and tear tissue during use. In addition, the user may experience resistance to piercing as a result of the presence of the needle opening. Furthermore, and perhaps more problematic, having an opening at the distal end of the needle may weaken the instrument and result in bending of the needle tip and possibly instrument failure.

Alternative instruments include a suture passer and suture retriever slidably received within the needle lumen. For example, a suture passer may utilize a pre-memory formed flexible wire, in the form of a ribbon of nickel-titanium alloy, for capturing suture. However, operation of such instruments may require a high degree of accuracy when it is used to capture a suture. The flexible wire may be controlled through the instrument handle.

Further instruments may utilize a wire loop that extends from a distal needle and can be used to capture a suture which has been advanced by the suture passer, which exits the instrument from a second opening in the needle of the same device. The passer may have a modified distal end to readily advance and disengage a suture after it has been captured in the loop of the retriever. The passer and retriever may be manipulated longitudinally and rotationally with respect to the instrument so that the suture retriever can be passed through the needle pierced through tissue to be sutured. Retracting the instrument will cause one end of the suture to be pulled back through the tissue. When capturing and retrieving suture with this device, suture is fixed at the distal end of the device.

A problem associated with at least some of these instruments is that they do not allow a suture to slide within the device while the suture is contained within the instrument. Suture slide is an advantage for some other styles of suture passing devices. For those instruments which do not allow suture to slide, the method of maintaining the captured suture is by clamping down on it, this creates an increased risk of damaging the suture. In addition, tissue snagging and tearing during the passing of suture, due to the large profiles required by these more complex instruments are also problems.

A more convenient arthroscopic approach could have considerable advantages if these obstacles were overcome. In particular, the provision of a low profile instrument which allows a captured suture to slide within the instrument without snagging and results in reduced tissue damage is desirable. Accordingly, there exists a need for a better arthroscopic approach.

SUMMARY OF THE DISCLOSURE

The present disclosure seeks to overcome at least some of the above issues by providing a surgical instrument which has the ability to capture, pass, retrieve suture, and thread suture within a joint, whilst also allowing the suture held within the instrument to slide. The instrument also provides a single point for piercing, and all other tissue and/or cartilage engaging surfaces are smooth. Also the distal piercing tip and respective tissue piercing face may be non-cannulated, thus providing for a repeatable and uninterrupted pierce.

According to the present disclosure, a surgical instrument is provided that in an example embodiment may include a shaft assembly, having a tubular member with a proximal end and a distal end, and a tip, e.g., a needle tip distal to the tubular member. Advantageously, the shaft assembly may further define a lumen e.g., extending between the proximal and distal ends. In some embodiments, the shaft may include a distal portion, having an opening in a side wall thereof (e.g., proximal to the tip). In example embodiments, the opening may be in communication with the lumen through the side channel. The surgical instrument may further include a handle component (e.g., connected to the proximal end of the shaft) and a suture snare, the snare being slidably receivable within the lumen and side channel, and movable between extended and retracted positions for capturing a suture.

Suitably, the side channel may be angled relative to the lumen axis. Preferably, the side channel includes at least one bend. Alternatively, the side channel is curved, or is curved and includes at least one bend. In example embodiments, the side channel may follow a path which deviates from the needle tip axis. In some embodiments, the side channel may follow a path which is substantially oriented with an outer edge of the needle tip (e.g., the outer edge of the needle and the side channel may be substantially parallel to one another). In other embodiments, the side channel may follow a path which is at an angle relative to the outer edge of the needle tip.

Suitably, the distal portion of the shaft may be curved. Alternatively, the distal portion of the shaft is bent, or comprises at least one bend and curved portion. The distal portion of the shaft may be curved and the opening may be located on an inside diameter of the curved distal portion. Alternatively, the distal portion of the shaft may be curved and the opening may be located on an inside diameter of the curved distal portion.

In some embodiments, a needle tip axis defined by a tapered portion of the needle tip may be substantially axially oriented with the shaft, e.g. with a proximal straight portion of the shaft or with a distal curved portion of the shaft. In other embodiments, an outer needle axis defined by an outer edge of the needle tip may be substantially axially oriented with the shaft, such as with an axis defined by a proximal straight region of the shaft or with an axis defined by a distal curved region of the shaft (e.g., at a distal end thereof). In some embodiments, the needle tip axis defined by the tapered portion of the needle may be substantially aligned relative to an outer diameter of the shaft, e.g., an outside diameter a distal end of a curved distal region of the shaft. In other embodiments, the needle tip axis defined by the tapered portion of the needle may be substantially aligned relative to an inner diameter of the shaft, e.g., an inside diameter a distal end of a curved distal region of the shaft. Preferably, the side channel diameter is smaller than the lumen diameter. Suitably, the lumen diameter is constant along its length. Alternatively, the lumen has a stepped diameter and includes two or more sections having different diameters. Preferably, the stepped diameter reduces distally.

The above features contribute to the snare projecting at an angle to the shaft when in an extended position. This allows a surgeon to sweep a wide area in order to capture a suture within a surgical site, reducing the technical demands for operating the instrument. In addition, the resulting snare projection trajectory helps to reduce the risk of suture pinching or trapping, and provides a more reliable extension each time the snare is used. The snare may be formed in the geometry of a hook. This hook feature may allow for suture to be captured and pulled back into the needle with minimal movement to the device needle tip and axis itself. Conventional devices have required the needle tip to be manipulated more precisely, such that the suture needed to be contained within the mouth of the suture passer in order to close and hold suture in the device. The snare being in the configuration of a hook allows for suture to be captured anywhere along the retraction path of the hook, and provides a much larger capture region for suture. Thus, a user would not be required to translate the device excessively while pierced through delicate tissue in order to capture suture, as the hook has a larger sweep area for suture capturing.

In example embodiments, the lumen may connect to a slot in a side wall of the shaft, the slot opening up into a recessed portion of the needle tip. The lumen may advantageously terminate at a distal portion of the recess and not extend through the distal end of the needle tip. In exemplary embodiments, the side walls of the slot and/or of the recess may enable proper seating and extension of the snare such as to prevent the snare from rotating when it is moved between the extended and retracted positions (e.g., by biasing the snare to remain in plane with a pre-bend thereof).

In some embodiments, at least a portion of the snare and at least one of the lumen and the side channel or slot/recess may include complementary non-circular cross sections to prevent the snare from rotating when it is moved between extended and retracted positions. Alternatively, the lumen and side channel or slot/recess may include any combination of circular and/or non-circular cross sections that are complementary to the snare. As a result, the snare alignment may be maintained due to the constraints within the device and the snare does not inadvertently rotate during use.

Fixing the relative angular position of the snare within the instrument may provide for a more stable instrument during manipulation of suture, and allows the technique to be repeated using the same instrument without any noticeable loss in performance. As a result of this arrangement, suture held within the instrument is more secure, and the risk of the instrument 'dropping' the suture is greatly reduced since the snare is unable to rotate.

In alternative embodiments, not shown, the snare may be rotatable about the instrument axis in a clockwise or counter-clockwise direction. Preferably, rotation is restricted to about 60 degrees, although it may be desirable that the angle of rotation is greater than or less than 60 degrees. Rotation of the snare may be controlled by a thumb actuator, which may incorporate features that allows the snare to be rotated in a clockwise or counter-clockwise direction by the users thumb manipulation. Rotating the thumb actuator in the handle would then rotate the snare in an intuitive manner. Alternatively, the thumb actuator could be split into left and right portions which can rotate the snare counter-clockwise or clockwise depending on which side of the thumb slide is actuated. Moving both sides of the actuator together could extend the snare without rotation.

Preferably, the snare includes a distal hook. Suitably, the instrument tip includes a recess adjacent to and distal of the opening. Preferably, the recess houses the snare hook when the snare is in the retracted position. This arrangement reduces the profile of the instrument and helps to minimise any damage caused when the instrument is pushed through tissue during suture passing.

Preferably, the tip is substantially solid. This arrangement provides no open cavities along the piercing edges, and thus helps to prevent tissue snagging, unwanted tissue removal, and any associated tissue damage in the surgical site. In addition, the solid tip provides strength and rigidity to the distal region of the instrument, reducing the likelihood of instrument failure and resulting in better tissue piercing capabilities.

Preferably, the instrument includes a passage extending transversely through the tip when the snare is in a fully retracted position, the passage formed between the snare hook and the recess of the tip. The passage allows a suture, captured in the instrument, to slide when the snare is in a fully retracted position. This ability for a captured suture to slide eliminates the need for additional instrumentation when performing certain surgical steps. Accordingly, the instrument provides the capability of suture capture, passing, and retrieval within a single instrument. This allows the instrument to be kept small and simple—generally, only fully extended and fully retracted positions of the snare are required—and all functionality is obtained through the same device.

Suitably, the snare is formed from stainless steel, nitinol, plastics, polymers, or any combination of the aforementioned. Preferably, the snare is formed from stainless steel. More preferably, the snare is formed from Type 302 Stainless Steel. The use of stainless steel is desirable from a strength perspective and helps to minimise the risk of the snare failing. As a consequence, the snare may be reliably and consistently deployed when extending/retracting over a number of cycles, and the risk of the snare buckling within the instrument is reduced. Optionally, the steel or nitinol may be tempered or heat treated in a number of ways suitable to the specific application. Optionally, the snare is formed from a material having shape-memory properties. In instruments in which the snare is deformed during deployment and retraction, the deformation path through the lumen and side channel is optimized so that the integrity and strength of the snare is maintained, so that the instrument can be used a number of times during a particular procedure. Preferably, the snare may be utilized as a spring, in that it is able to fully extend when in the open position, but then conforms to the shape of the inner lumen when retracted into the closed position. Suitably, this spring characteristic may enable/facilitate the snare closing into the needle tip.

Suitably, the snare includes a coating such as PTFE or a silicon based lubricant to facilitate actuation of the snare. Preferably, a coating or surface hardening treatment such as ME-92, MEDCOAT 2000, or Kolsterising is used which increase the surface hardness of the snare material and reduce any galling that may occur between the interacting metal components. Alternatively, the side channel surfaces, or the snare and side channel surfaces include such coatings or treatments. Preferably, the handle is an in-line handle and includes a thumb actuator for moving the snare between the extended and retracted positions. Alternatively, the handle is a pistol-grip handle. According to such embodiments the trigger mechanism may be coupled about a pivot point to the proximal end or a proximal region of the snare assembly.

Suitably, the instrument includes a lock for locking the position of the snare relative to the shaft, particularly when the snare is in a retracted or stowed position. The lock helps to ensure that the snare does not move by accident when, for example, a suture is captured within the instrument, which may result in the suture being dropped. In addition, the lock may ensure that user does not inadvertently deploy the snare while piercing through the tissue. Suitably, the thumb actuator may include two positions—a snare extended position for capturing suture and a snare retracted/locked position, e.g., in which a captured suture is freely slidable and/or in which the trigger mechanism may be locked such as to prevent the snare from accidentally being moved to the snare extended position. In some embodiments, the thumb actuator may include three positions—a snare extended position for capturing suture, a snare retracted position in which a captured suture is freely slidable, and a suture locked position, e.g., which may clamp down on the suture and prevent it from sliding. The suture locked position and/or the snare retracted position may include a safety mechanism for locking the snare and preventing accidental extension thereof, e.g., during insertion of the needle. Example locking mechanisms which may be employed include groves or slots, e.g., associated with a particular position of the snare/and or of a trigger mechanism or handle for the snare. In some embodiments, a ratchet type mechanism may be employed. Preferably, the lock may include an audible or tactile feedback mechanism when the snare is moved between locked and unlocked positions.

BRIEF DESCRIPTION OF THE DRAWINGS

The above and other aspects, features and advantages of the disclosure will be apparent from the following more particular description of examples, as illustrated in the accompanying drawings, in which:

FIG. 1 is an isometric view of an embodiment of an instrument, according to the present disclosure;

FIG. 2 is an expanded view of the embodiment of FIG. 1, according to the present disclosure;

FIG. 4 is a close-up isometric view of the distal end of the embodiment of FIG. 1 with a section of snared suture, according to the present disclosure;

FIGS. 5A and 5B are close-up views of the tip of the embodiment of FIG. 1, according to the present disclosure;

FIG. 18 is a side view of a further example embodiment of a distal end of a suture passer instrument, the example embodiment illustrating a slot in a distal end of a distal curved region of a shaft of the suture passer instrument and a snare with a pre-bend, wherein an outer needle axis defined by an outer edge of a needle tip of the suture passer instrument is substantially axially oriented with an axis defined by a proximal straight region of a shaft of the suture passer instrument, according to the present disclosure;

FIG. 19A is a side view of a further example embodiment of a distal end of a suture passer instrument, the example embodiment illustrating a slot in a distal end of a distal curved region of a shaft of the suture passer instrument and a snare with a pre-bend, according to the present disclosure, according to the present disclosure;

FIG. 19B is a magnified side view of the slot in the distal end of the distal curved region of the shaft of the suture passer instrument of FIG. 19A, according to the present disclosure;

FIG. 19C is a side view of the distal end of the suture passer instrument of FIG. 19A, illustrating clearance of the snare relative to a needle tip of the suture passer instrument, according to the present disclosure;

FIGS. 20A-20D illustrate an example relationship between an exit position of the snare of FIG. 19A (e.g., as impacted, in the open and/or closed position, by the length of the slot, angle of the shaft relative to a needle tip, shape of the needle tip, formed geometry of the distal end of the snare and/or the pre-bend of the snare) and various concern areas for the potential for cleating, according to the present disclosure;

DETAILED DESCRIPTION

Figure 3A:
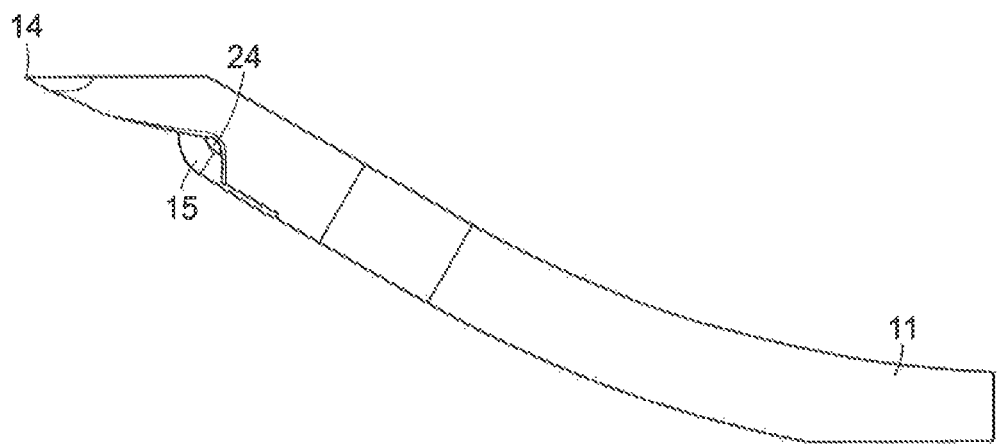
FIGS. 3A and 3B are close-up side views of the distal end of the embodiment of FIG. 1, according to the present disclosure.

In the description that follows, like components have been given the same reference numerals, regardless of whether they are shown in different examples. To illustrate an example(s) of the present invention in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and in the claims, the singular form of "a", "an", and "the" include plural referents unless the context clearly dictates otherwise.

As used in the specification and in the claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue.

Referring to FIGS. 1 and 2, there is shown a suture passer 10 having an elongate shaft 11 extending distally from a handle 12. Shaft 11 includes a curved distal region 13 and a pointed needle tip 14. In the embodiment shown the curve is angled at around 30 degrees (e.g., 24 degrees) to the proximal region of the shaft, and oriented upwards. Other angles may be employed in alternative instruments. In alternative embodiments, not shown, the distal region is bent instead of being curved, or may include bent and curved regions. In a further alternative embodiment, not shown, the shaft and distal region are straight.

Handle 12 is an in-line type handle. Handle 12 may, in some embodiments, include an opening 17 for accommodating a user's fingers. In alternative embodiments, the handle does not include such an opening, and the user's fingers simply fit around the handle. The handle 12 may also include an actuator 16 in the form of a thumb activated slider which may be moved distally away from the handle 12 to activate the instrument. In some embodiments, not shown, the actuator may be biased by suitable means, such as a spring, to default to a particular position when an application force is removed, for example, when a user removes pressure from a finger or thumb. In alternative embodiments, not shown, the handle may be of the pistol-grip type.

Figure 3B:
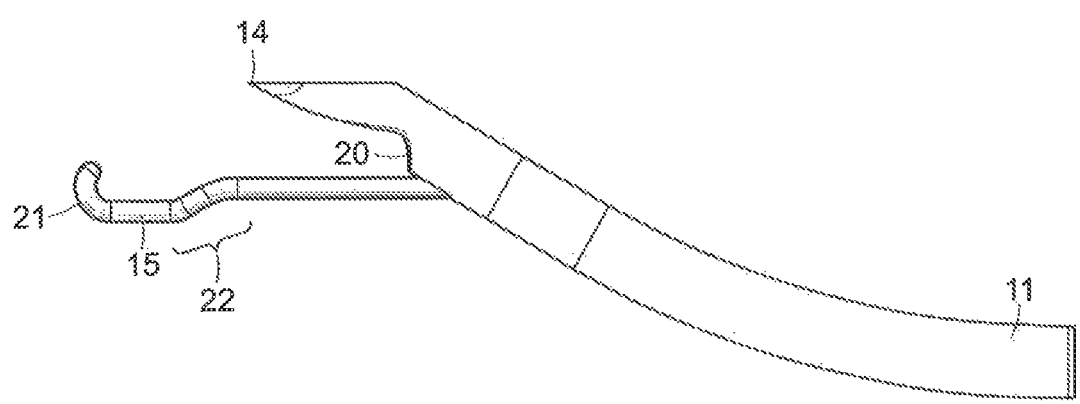

Referring now to FIGS. 3A and 3B, the suture passer includes a suture snare 15 which is slidably received within the lumen of tubular shaft 11 and extendable therefrom. According to this arrangement, and as shown in FIG. 3B, when the snare 15 is advanced distally by means of actuator 16, as will be described in greater detail below, a portion of the snare 15 projects from the tubular member and can be used to capture a suture (not shown). The snare can then be retracted to the position shown in FIG. 3A (also see FIG. 4). In embodiments where the actuator is biased, this may be achieved by removing the force of the user's finger or thumb, depending on the relative orientation of the bias.

Figure 6:
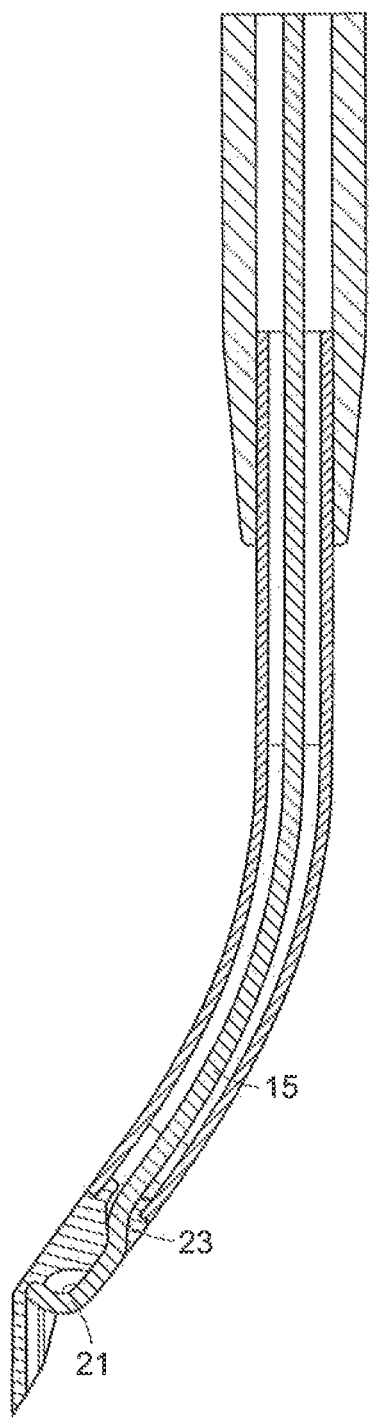
FIG. 6 is a sectional side view of the distal end of the embodiment of FIG. 1, according to the present disclosure.

Shaft 11 is formed from a substantially solid needle tip 14 and one or more coaxial tubular members extending proximally from the solid tip to the proximal end of the shaft (see FIG. 6). This arrangement makes use of a closed off distal tip which prevents suture entrapment in the end of the needle and provides strength in the piercing portion of the needle. The solid tip also presents unbroken piercing edges and helps to prevent snagging and tearing, and the unwanted removal of tissue from the surgical site (FIGS. 5A & 5B). In the embodiment shown, the needle tip 14 is welded to the distal end of the tubular member to form shaft 11. Alternatively, the tip 14 may be formed integrally with the tubular portion of the shaft, or attached by means such as crimping, swaging, or crushing the end of the proximal tube to create a solid distal tip.

Figure 7A:
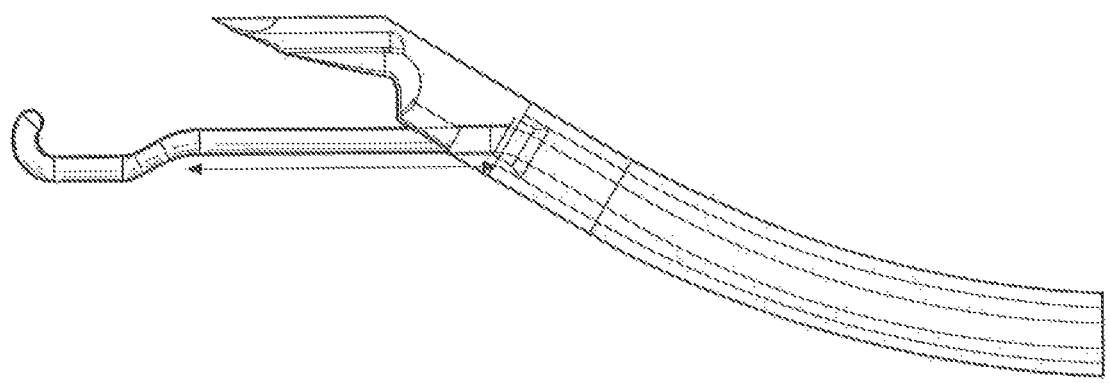
FIGS. 7A and 7B are side views of FIG. 3, where the needle and tubing members are shown in a transparent view, according to the present disclosure.

As depicted in FIGS. 6 and 7, the shaft 11 includes an opening (not shown) in a sidewall of the shaft, proximal to the needle tip 14, the opening being in communication with the lumen of the shaft through side channel 23. In the illustrated embodiment, the side channel 23 is bent at an angle to the axis of the lumen (in example embodiments, the side channel may be at approximately a 30 degree angle relative to an axis of the needle tip or approximately 150 degrees relative to an axis of the lumen). In alternative embodiments, not shown, the channel is curved or may comprise one or more bends and/or curved sections. Accordingly, the tubular member and side channel provide a passage through the instrument which extends from the proximal end of the instrument shaft to the opening.

As shown in FIGS. 3A and 3B, the needle point 14 is oriented to the outside diameter of the curved distal region 13 of the instrument shaft. In alternative embodiments, not shown, the tip may be oriented axially with the shaft, or towards the inner diameter. The tip, which is formed as a substantially solid component, includes a recess or mouth 20 which surrounds the opening and provides access to the side channel in the curved distal region of the instrument.

As discussed above, the suture passer 10 includes a suture snare 15 housed within the shaft lumen (see FIGS. 7A and 7B), which is slidably extendable therefrom, as depicted in FIG. 3B. The distal end of the snare 15 includes a hook 21 for capturing a suture in use, and a kinked region 22 proximal of the hook 21. The kinked region has a shape that generally complements the shape of the channel 23, and which allows the hook 21 to fit snugly within the recess 20 when the snare is in a fully retracted position, as shown in FIG. 3A. The kinked region may advantageously result in suture captured within the snare being pushed away from the instrument shaft when the snare is deployed and moved to an extended position. Also shown FIG. 3A is a transverse passage 24 which is created between the hook 21 and recess 20 of needle tip 14 when the snare 15 is in a fully retracted position. In use, the transverse passage 24 permits a suture, captured in the instrument, to slide when the snare is positioned accordingly. To provide a surgeon with a degree of control over the rate at which the suture may slide, it may be desirable that the suture is subjected to a small amount of resistance or drag when captured within passage 24. The ability of a captured suture to slide is advantageous as it removes the need for additional instrumentation when performing certain surgical steps. Thus, the instrument provides a surgeon with the ability to capture, pass and retrieve suture, all without the need to change instrumentation, which is particularly advantageous in arthroscopic procedures. The instrument can therefore be kept small and relatively simple, as only two positions for the snare are necessary—fully extended and fully retracted.

As will be appreciated, various needle recess geometries could be designed to mate with the hook, and these could be used to control the degree of drag that exists when the suture is sliding. In addition, the surfaces of the hook, the recess or both the recess and hook may be textured to provide resistance to the suture. Alternatively, the respective surfaces may be highly polished or may be coated with a friction reducing material to enhance suture sliding. Further, one or more of the respective surfaces may include a coating such as PTFE or a silicon based lubricant to facilitate movement of the snare within the instrument shaft.

In further alternative embodiments, not shown, the instrument includes an additional retracted position in which the suture is held fast, and unable to slide—such embodiments provide a multi-positional actuator mechanism that allows for open, suture slide, and closed positions.

Figure 7B:
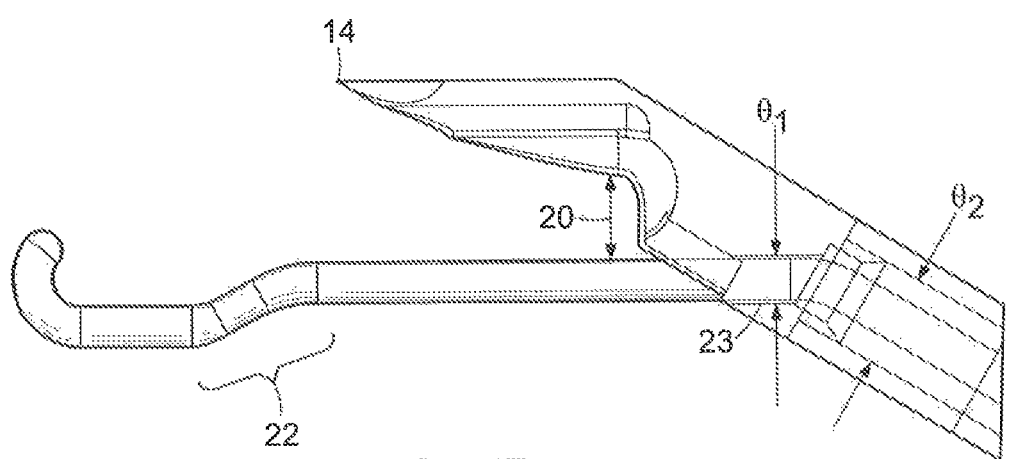
Figure 8:
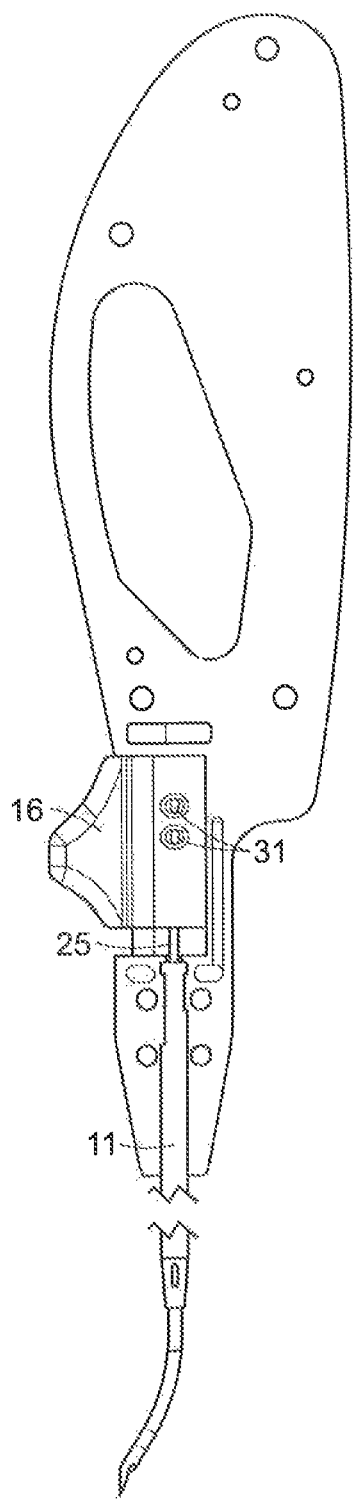
FIG. 8 is a side view of FIG. 2 with one half of the handle removed for visualization into the inner workings of the instrument, according to the present disclosure.
Figure 9:
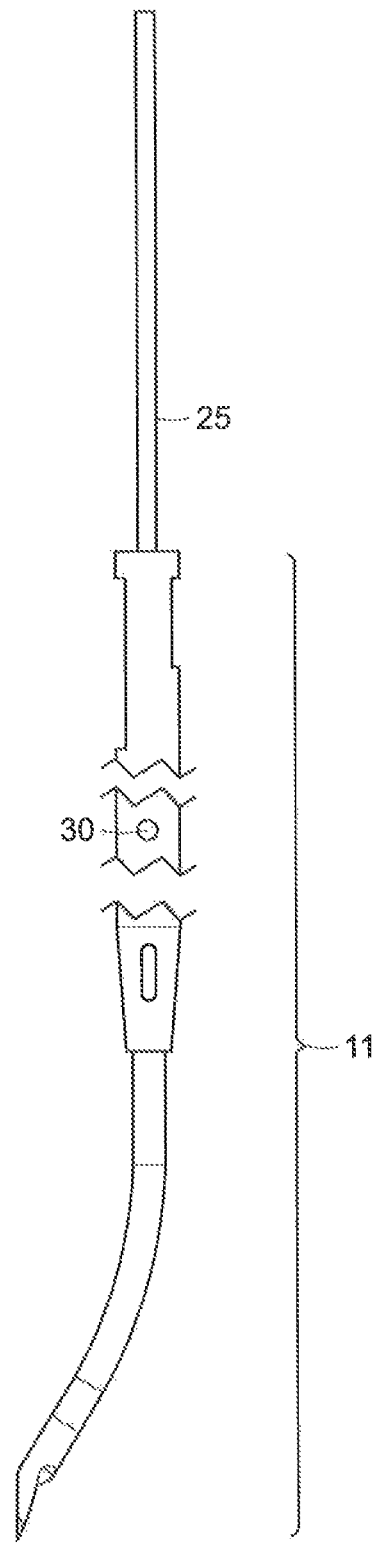
FIG. 9 is an exploded view of the instrument shaft of FIG. 1, where the outer tubular members are shown in a transparent view, according to the present disclosure.

Referring now to FIG. 7B, channel 23 has a diameter $\theta_1$ which is smaller than the diameter $\theta_2$ of the lumen, and the snare 15 is dimensioned to have a close tolerance with the channel 23 (e.g., a tolerance less than 20%, more desirably less than 15% and most desirably less than 10%). The close tolerance between channel 23 and the snare 15 causes the snare to project away from the shaft 11 at a desired trajectory. As a result, this greatly reduces the severity of any 'wedge' effect which is experienced—whereby suture may become trapped between the snare and instrument shaft. The wedge effect generally occurs when the suture is already captured within the instrument, and the snare is in a retracted position. This may be pre- or post-tissue piercing, and arises when extending the snare, and when the distance between the snare and needle tip is too small to accommodate the suture and thus, the suture may become wedged or cleated in the instrument. It may also occur during passage through tissue when a suture has been captured and the snare is in a retracted position. In this situation, as the instrument is passed through tissue, a tension is imposed on the suture in the direction opposite to that of the piercing. The features described above in relation to FIG. 7B help to reduce these effects, allowing the suture to be easily released when the snare is extended. Additionally, this arrangement makes the instrument easier to use by increasing the effective area in which suture can be snared.

In the embodiment shown, the lumen and side channel have circular cross sections. However, in alternative embodiments it is desirable to positively prevent rotation of the snare relative to the instrument shaft when it is moved between extended and retracted positions. Accordingly, at least a portion of the lumen or side channel (or both), and at least a portion of the snare are formed with complementary non-circular cross sections to prevent rotation of the snare during its deployment.

As mentioned above, the diameter of the snare 15 is slightly smaller than the diameter $\theta_1$ side channel 23, to provide a close fit within the channel. However, because the diameter $\theta_2$ of the lumen is larger there may be a tendency for the snare to buckle within the lumen under high loads. To prevent this, the lumen can be formed with a smaller diameter. Alternatively, the snare can be formed with a stepped diameter, which is larger towards the proximal end of the instrument and reduces in diameter in one or more steps towards the distal end of the instrument. These different arrangements each provide a tighter fit between the instrument components within the lumen to reduce the possibility of the snare buckling under loading.

Figure 10:
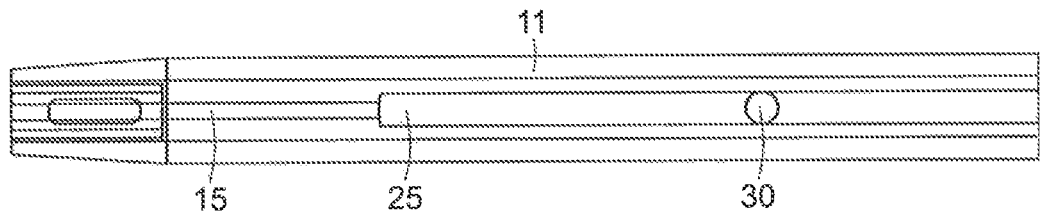
FIG. 10 is a close-up sectional side view of the instrument shaft of FIG. 1, according to the present disclosure.
Figure 11:
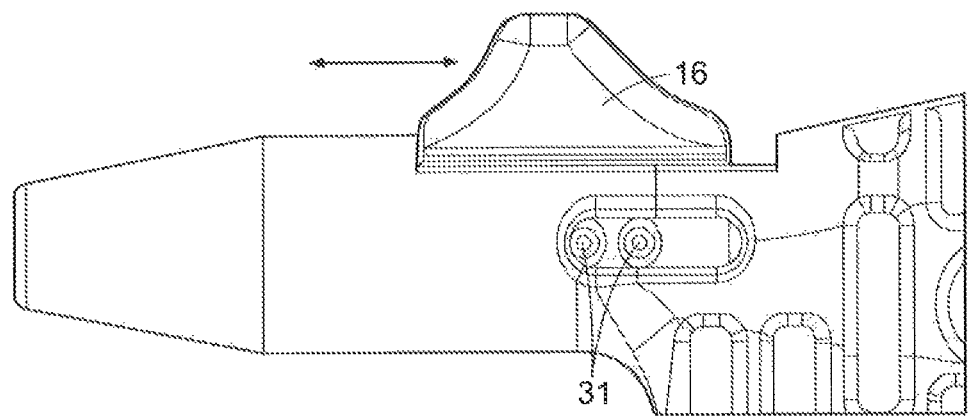
FIG. 11 is a close-up side view of an actuator button of FIG. 1, according to the present disclosure.

A further alternative solution to the above issue is described in relation to FIGS. 8 to 11. As best shown in FIG. 10, a snare sleeve 25 is slid over snare 15 and crimped to it at distal and proximal crimping locations 30 and 31, respectfully. This particular form of assembly prevents the need for welding, and allows for a clean room assembly using crimping operations. Briefly, the instrument may be assembled by first inserting the snare proximally through the shaft, through the distal opening. The snare sleeve is subsequently slid distally, over the proximal end of the snare and from the proximal end of the instrument. The snare and snare sleeve are then appropriately aligned before being crimped together at the proximal and distal locations illustrated in FIGS. 9 to 11. With regard to the distal crimping location, holes 30 are provided in the instrument shaft so that a suitable crimping instrument can engage the holes to provide the necessary compressive crimping force. With regard to the proximal crimping location, suitable holes may be provided in the thumb actuator area, or crimping can be accomplished before attaching the handle to the device. As will be appreciated, this is just one manner in which the instrument components may be assembled and crimped, and other possibilities will be appreciated.

In addition, the instrument incorporates an ergonomic handle that is formed to fit the grasping shape of a surgeon's hand. As described above, the thumb actuator in the handle is located in a position that is easy to use. The snare hook may be extended by pushing the button forward, and retracted by pulling the button back. These motions are intuitive and simple for the user to carry out.

Figure 12:
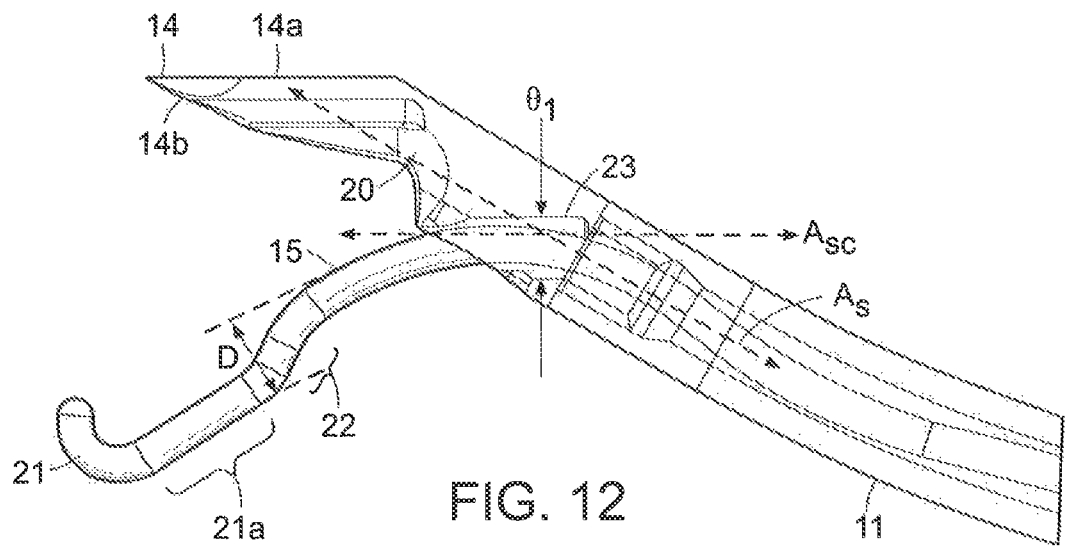
FIG. 12 is a side view of a further example embodiment of a distal end of a suture passer instrument, the example embodiment illustrating a wide tolerance side channel and a snare with a pre-bend, according to the present disclosure.

With reference to FIG. 12, a further example embodiment of a distal end of a suture passer instrument is depicted. The example embodiment illustrates use of a wide tolerance side channel 23 and a suture snare 15 with a pre-bend. In particular, in contrast, e.g., with the embodiment illustrated in FIG. 7B, the side channel 23 in FIG. 12 has a diameter $\theta_1$ which substantially larger than the diameter of the suture snare 15. For example, in some embodiments, the diameter $\theta_1$ of the side channel may be greater than 1.25, 1.5, 1.75, 2, or 2.5 times the diameter of the suture snare. In some embodiments, the diameter $\theta_1$ of the side channel may be approximately 0.02 to 0.04 inches and the diameter of the suture snare may be approximately 0.01 to 0.02 inches. In example embodiments, the diameter $\theta_1$ of the side channel 23 may be configured to be approximately the same as the diameter of a lumen of a shaft 11 of the suture passer instrument. In general, the wide tolerance of side channel 23 at diameter $\theta_1$ may advantageously allow for a less tortuous path for suture snare 15 to travel and deform, e.g., thereby reducing frictional forces and galling. Notably, lubricating coatings (such as a silicon based liquid) or surface hardening techniques such as ME-92, may be applied to further reduce galling. The use of a pre-bend with respect to the suture snare 15 advantageously increases the kick-out clearance of the snare 15 relative to the shaft 11 and needle tip 14 of the suture passer instrument.

In example embodiments, the diameter $\theta_1$ of the side channel 23 may be configured to be less than an offset distance D of a hook end 21 of the suture snare 15 as determined by a kinked region 22 of the suture snare (e.g. less than (e.g. 0.9, 0.8, 0.7, 0.6, or 0.5 times the offset distance D). In this way, a kinked region 22 of the snare 15 (which may generally have a same length as the side channel 23) may cause the hook end 21 to pivot (e.g., in plane with the kinked region 22 and the diameter $\theta_1$) so as to allow the hook end 21 to fit securely within a recess 20 of a needle tip 14 when the snare 15 is in a retracted position (see, e.g., the embodiment of FIG. 3A). In some embodiments, the suture passer instrument (e.g., the side channel 23 and/or the snare 15) may be configured such that an offset region 21a (e.g., an offset elongated region) of the hook end 21 is substantially parallel to an axis $A_c$ of the side channel 23 prior to the kinked region 22 entering the side channel 23 during retraction of the snare 15. Moreover, in some embodiments, the suture passer instrument (e.g., the side channel 23 and/or the snare 15) may be configured such that the offset region 21a of the hook end 21 is pivoted to be substantially parallel to an axis of the $A_s$ of a shaft 11 (such as an axis defined by a proximal straight region of the shaft or an axis defined by a distal curved region of the shaft e.g., at a distal end thereof) when the snare 15 is in a retracted position and the kinked region 22 is retracted into the side channel 23.

In example embodiments, such as illustrated in FIG. 12, the needle tip 14 may define an outer edge 14a which may be configured to be substantially parallel with the axis $A_c$ of the side channel 23. Thus, in some embodiments, the outer edge 14a of the needle tip 14 may be at an angle relative to the an axis $A_s$ of the shaft, e.g., at a distal end thereof. In some embodiments, the shaft 11 may include a distal curved region. Thus, in some embodiments, the outer edge 14a of the needle tip 14 may be substantially parallel with an axis of the shaft at a proximal end thereof and at an angle relative to an axis of the shaft at a distal end thereof. In further example embodiments, the needle tip 14 may define a tapered region 14b (e.g., a tapered plane) which may be configured to be substantially parallel with an axis $A_s$ of the shaft, e.g., at a distal end thereof. Notably, the tapered region/plane 14b may in some embodiments define a distal end wall of the lumen. In other embodiments, the lumen may extend through the tapered region/plane. In yet other embodiments the lumen may end at a distal region of the slot or of the recess (e.g., at a distal lip of the recess).

With reference still to FIG. 12, in example embodiments, the side channel 23 may have a first diameter $\theta_1$ of the side channel 23 characterizing a wide tolerance and a second diameter perpendicular to the first diameter characterizing a narrow tolerance. In this way, the side channel 23 may prevent/resist the suture snare 15 from rotating in the side channel, e.g., by biasing the pre-bend of the snare 15 to remain in plane, e.g., with the outer edge 14a of the needle tip and perpendicular to the tapered plane 14b of the needle tip 14.

Figure 13:
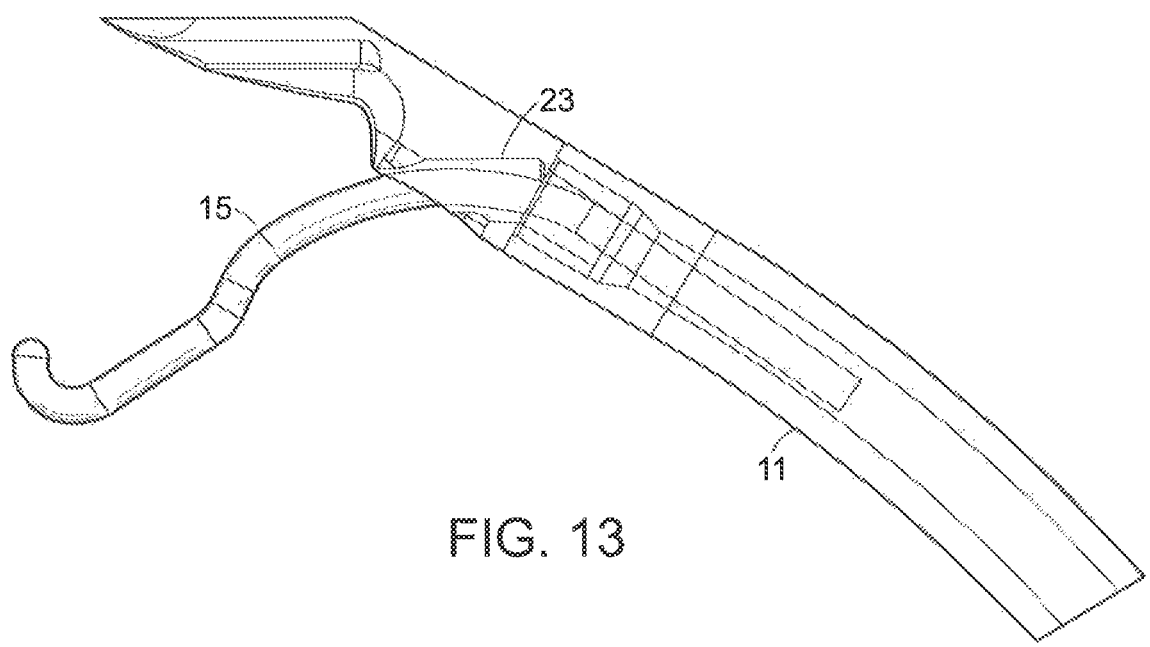
FIG. 13 is a side view of a further example embodiment of a distal end of a suture passer instrument, the example embodiment illustrating a wide tolerance side channel and a snare with a pre-bend, wherein a curved distal region of a shaft of the suture passer instrument is aligned with the pre-bend of the snare and the with the side channel, according to the present disclosure.

With reference now to FIG. 13, a further example embodiment of a distal end of a suture passer instrument is depicted. The example embodiment again depicts use of a wide tolerance side channel 23 and a suture snare 15 with a pre-bend. The embodiment of FIG. 13 advantageously illustrates aligning a curved distal region of the shaft 11 of the suture passer instrument with the pre-bend of the snare 15 and with the side channel 23. In particular, the shaft 11 is configured such that the curved distal region curves in the same direction as the pre-bend in the snare 15 and the branch direction of side channel 23. This alignment of the curved distal region of the shaft 11 with the pre-bend of the snare and with the side channel 23 advantageously further reduced galling, e.g., relative to the embodiments depicted in FIGS. 7A, 7B and 12.

Figure 14:
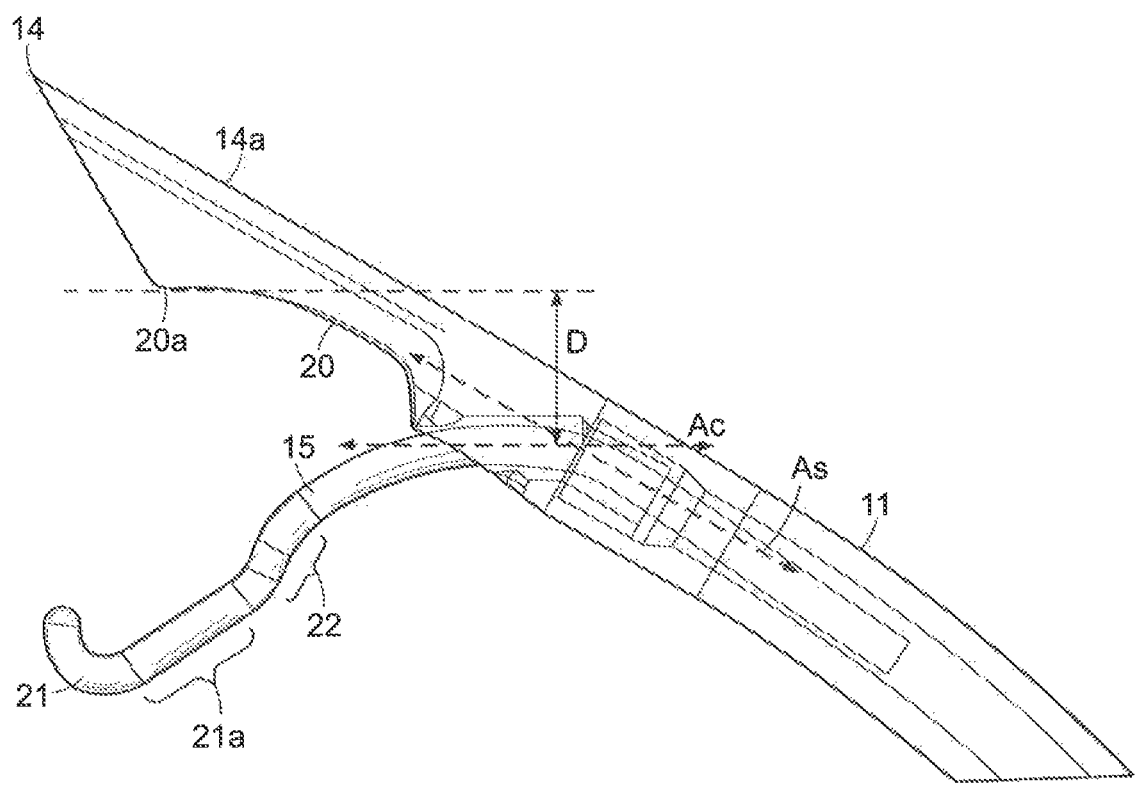
FIG. 14 is a side view of a further example embodiment of a distal end of a suture passer instrument, the example embodiment illustrating a wide tolerance side channel and a snare with a pre-bend, wherein an outer needle axis defined by an outer edge of a needle tip of the suture passer instrument is substantially axially oriented with an axis defined by a distal curved region of a shaft of the suture passer instrument at a distal end thereof, according to the present disclosure.

With reference now to FIG. 14, a further example embodiment of a distal end of a suture passer instrument is depicted. The example embodiment again depicts use of a wide tolerance side channel 23 and a suture snare 15 with a pre-bend. FIG. 14 illustrates the outer edge 14a of the needle tip 14 being configured to be substantially parallel relative to an axis $A_s$ of the shaft, e.g., at a distal end thereof. Notably, the configuration of the outer edge 14a in FIG. 14 provides for increased kick-out clearance of the snare 15 relative to the shaft 11 and needle tip 14 of the suture passer instrument (as compared with the embodiments of FIGS. 12 and 13). Notably, the recess 20 of the embodiment of FIG. 14 may define a trough region with a lip 20a. In example embodiments, lip 20a may be configured such that the perpendicular distance D between the axis $A_c$ of the side channel and the lip 20a is close enough to enable the hook end 21 of the snare 15 to securely fit in the recess 20 when the snare 15 is retracted. In example embodiments, the recess 20 may be configured such that the lip 20a is a perpendicular distance D from the axis $A_c$ of the side channel that is less than or equal to the perpendicular distance from the axis $A_c$ between the exit location of the snare 15 from the side channel 23 and the opposite side of the shaft 11. Note that similar to the embodiments of FIGS. 7A and 12, the snare 15 of the embodiment illustrated in FIG. 14 includes a kinked region 22 for enabling pivoting, e.g., of the offset region 21a of the hook end 21 of the snare 15 to better engage with the recess 20 such as when the hook is in a closed position.

Figure 15:
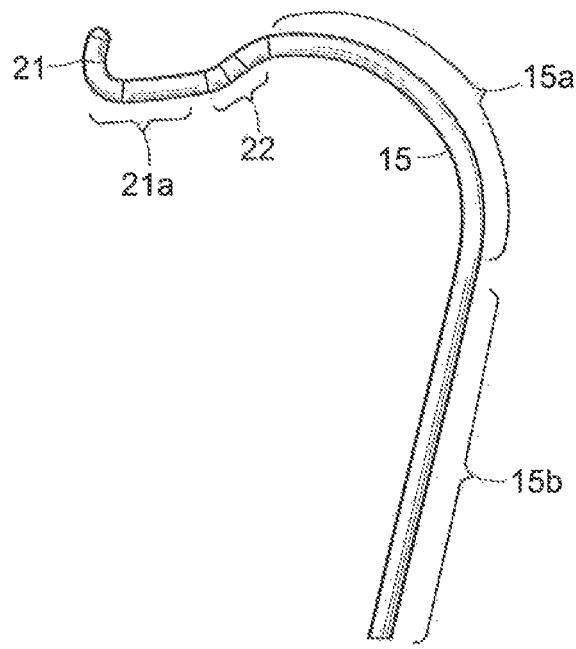
FIG. 15 is a side view of an example embodiment of a snare with a pre-bend, according to the present disclosure.
Figure 22A:
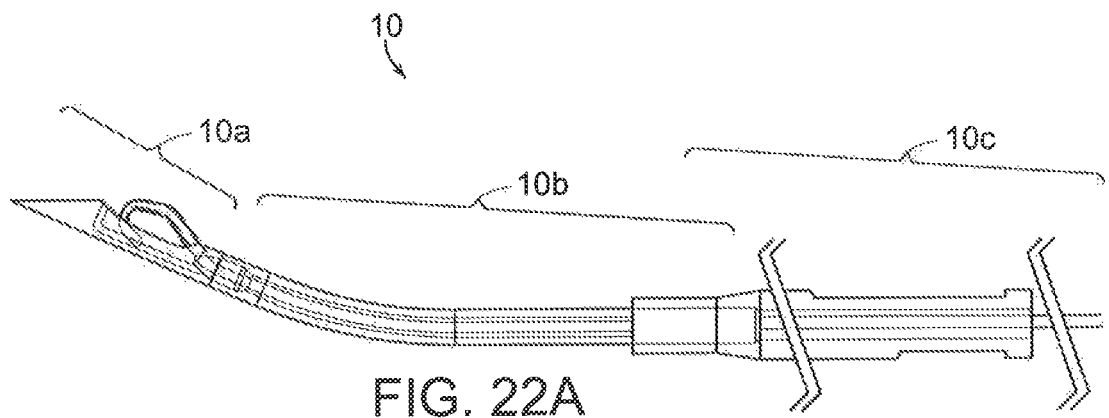
FIGS. 22A-22D illustrate an example manufacturing process, according to the present disclosure, for manufacturing example suture passer instruments such as disclosed herein.

With reference now to FIG. 15 an example embodiment of a snare 15 with a pre-bend is depicted. The snare 15 of FIG. 15 may include a pre-bend region 15a that includes an elastic bias toward a pre-bent curve. In some embodiments, the snare 15 may further include a proximal non-curved region 15b. As noted in previous embodiments, the snare 15 may also include a kinked region 22 for providing an offset for a hook end 21 of the snare. Thus, the snare 15 may define an offset region 21a of the hook end 21. The kinked region 22 may be longer, or at different angles/lengths than depicted and disclosed. This kinked region 22 can also act in the manner of a leaf spring which helps to close the hook into the needle tip in configurations similar to FIG. 22A. In example embodiments, the snare 15 may be constructed from a memory shape alloy material. In some embodiments the snare 15 may be constructed from 302 stainless steel, spring steel or a similar material.

Figure 16:
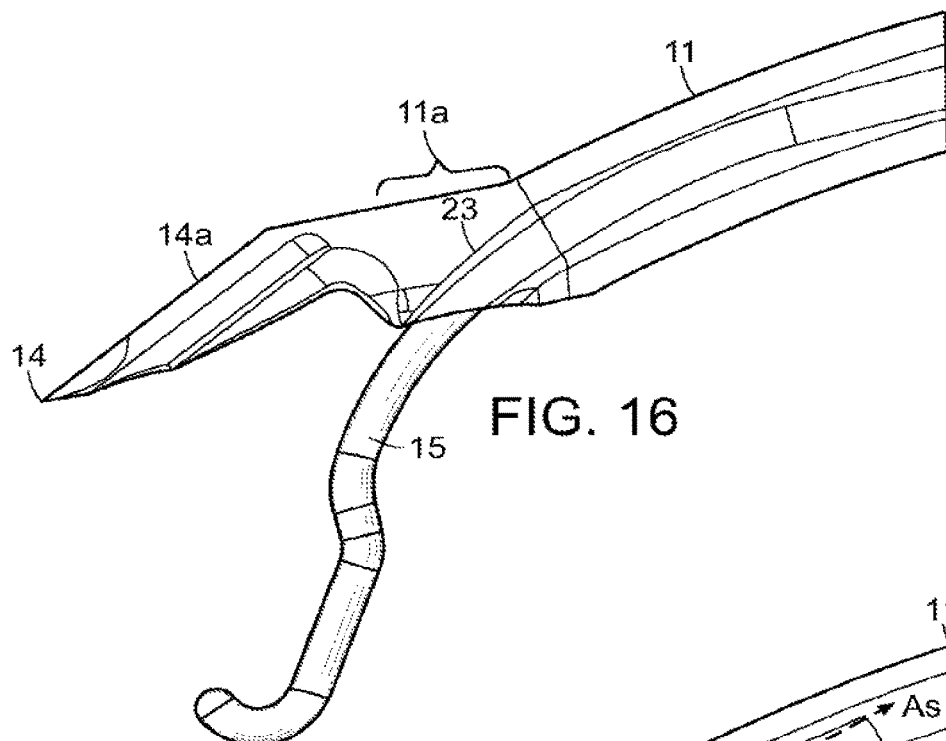
FIG. 16 is a side view of a further example embodiment of a distal end of a suture passer instrument, the example embodiment illustrating a wide tolerance side channel and a snare with a pre-bend, wherein the side channel is curved to substantially match a distal curved region of a shaft of the suture passer instrument, according to the present disclosure.

With reference now to FIG. 16, a further example embodiment of a distal end of a suture passer instrument is depicted. The example embodiment again depicts use of a wide tolerance side channel 23 and a suture snare 15 with a pre-bend. FIG. 16 advantageously illustrates a curved side channel 23. Notably, the curved side channel 23 of FIG. 16 is configured to substantially match the curve of the lumen of the shaft 11 at the curved distal region thereof. Thus, as depicted, the lumen of the shaft 11 may smoothly transition into the side channel 23, e.g., thereby further reducing the effects of galling. In example embodiments, this may be achieved, e.g., incorporating a bent region 11a of the shaft 11 distal to the curved region of the shaft (e.g., wherein the bend direction in the bent region 11a shaft 11 is opposite the curvature of the curved region of the shaft 11). In some embodiments, the bent region 11a of the shaft 11 may be substantially parallel to a proximal straight region of the shaft (not depicted). In some embodiments, the length of the bent region of the shaft may be determined by the length of the side channel 23. As depicted, the bent region 11a of the shaft 11 may transition into the needle tip 14 of the suture passer instrument. Thus, e.g. the needle tip 14a may define an outer edge 14a which may be configured to be substantially parallel with an axis of the side channel 23 (e.g., at a distal or proximal end thereof) or substantially parallel with an axis of the shaft (e.g., at the bent region 11a or at a proximal straight region thereof).

Figure 17A:
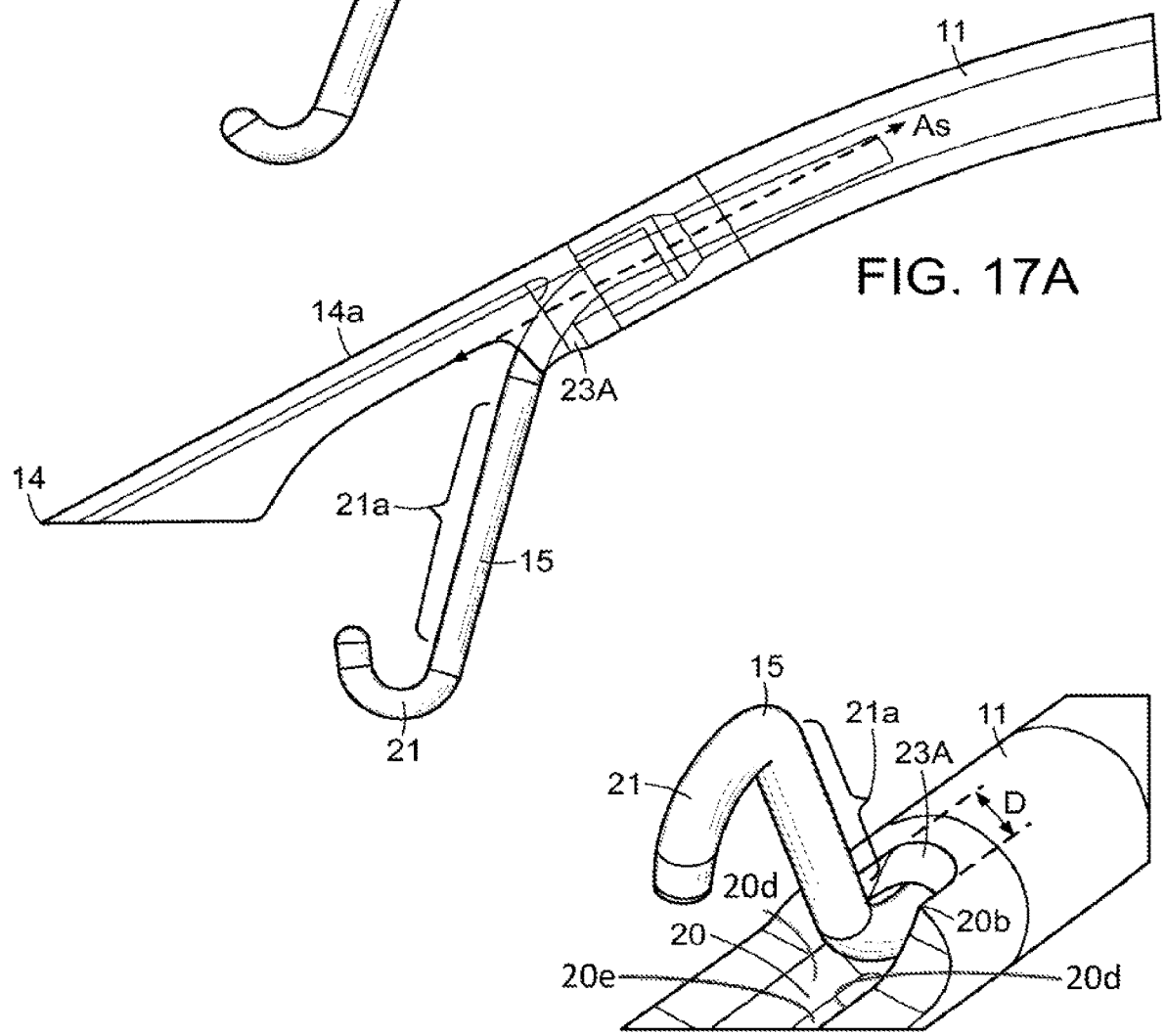
FIG. 17A is a side view of a further example embodiment of a distal end of a suture passer instrument, the example embodiment illustrating a slot in a distal end of a distal curved region of a shaft of the suture passer instrument and a snare with a pre-bend, according to the present disclosure.
Figure 17B:
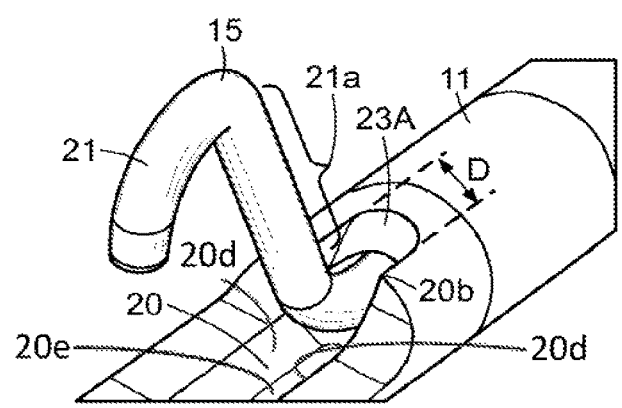
FIG. 17B is a perspective view of the slot in the distal end of the distal curved region of the shaft of the suture passer instrument of FIG. 17A, according to the present disclosure.

With reference now to FIGS. 17A and 17B, a further example embodiment of a distal end of a suture passer instrument is depicted. The embodiment of FIGS. 17A and 17B is similar to the embodiment of FIG. 14, except that the side channel 23 of FIG. 14 has been replaced with a slot 23a defined in the side wall of the shaft 11 and flowing directly into the trough of the recess 20. The trough is a cutout region defined by two diagonal sidewalls 20d cut into the sidewall of the shaft 11 which define a bottom 20e of the trough. The diagonal sidewalls 20d, and therefore the trough, run parallel to a length of the shaft 11. The use of the slot as opposed to a channel may advantageously further reduce the effects of galling. Notably, the width D, of the slot 23a as well as the width of the side walls of the recess (particularly at a proximal lip 20b of the recess 20) may be configured so as to exhibit a narrow tolerance relative to snare 15, thereby preventing/resisting rotation of the suture snare (e.g., by biasing the pre-bend of the snare 15 to remain in plane with the diagonal sidewalls 20d of the recess 20 and slot 23a to keep the snare 15 between the slot 23a and the bottom 20e of the trough). As depicted, the outer edge 14a of the needle point 14 in FIGS. 17A and 17B is substantially parallel to an axis $A_s$ of the shaft 11 at distal end of the curved region thereof. One other notable difference between the embodiment depicted in FIGS. 17A and 17B and the embodiment illustrated in FIG. 14 is the shape of the snare 15. In particular, snare 15 in FIGS. 17A and 17B does not include a kinked region. Furthermore, the hook end 21 of the snare 15 includes an elongated straight region 21a. In some embodiments, the elongated straight region 21, or the curved region of the snare 15 leading up thereto, a may be utilized in a leaf spring manner to ensure that the hook end 21 of the snare is always pushed down into the bottom of the needle tip recess 20, and thus is never biased towards the open position of the snare. Alternative embodiments may utilize a snare kink region as the leaf spring mechanism to ensure the snare consistently closes, and the remaining geometry of the snare mates adequately with the needle tip for other functional requirements of the device to be met. An example of this configuration can be seen in FIGS. 22a and 22c.

With reference now to FIG. 18 a further example embodiment of a distal end of a suture passer instrument is depicted. Similar to the embodiment of FIGS. 17A and 17B, the embodiment of FIG. 18 includes a slot 23a defined in through a side wall of the shaft 11 and flowing directly into the trough of the recess 20. Unlike in the embodiment of FIGS. 17A and 17B, the outer edge 14a of the needle tip 14 in FIG. 18 is angled relative the distal end of the curved region of the shaft, e.g., thereby increasing the clearance of the snare 15. Notably, the outer edge 14a may be configured to be substantially parallel to an axis of the shaft 11 at proximal straight (elongated) region distal thereof. The depicted embodiment of FIG. 18 also includes a pre-bent snare 15 with a kinked region 22 that advantageously enables pivoting of the hook end 21 of the snare 15 similar to as noted previously. In particular, the kinked region may interact with a mouth 23 b of the lumen of the shaft to cause the hook end 21 to pivot (e.g., such that an offset region 21a of the hook end 21 is parallel with the outer edge 14a of the needle tip 14.

With reference now to FIGS. 19A-19C a further example embodiment of a distal end of a suture passer instrument is depicted. The embodiment of FIGS. 19A-19C is similar to the embodiment of FIGS. 17A and 17B and includes a slot 23a defined in the side wall of the shaft 11 that flows directly into the trough of the recess 20. The embodiment of FIGS. 19a and 19b, however, depicts a different snare 15 with a hook head 21 that includes an spacing region 21a (depicted as an elongated spacing region which may be angled relative to a distal curved region or kinked region of the snare 15, e.g., such that the elongated spacing region is substantially parallel relative to the outer edge 14a of the needle tip 14). Notably, this configuration may allow for the curved or kinked region of the snare to act as a leaf spring and repeatedly pivot and/or compress the hook head 21 into the bottom of the needle tip recess when the snare is moved to the closed position. Advantageously, the snare 15, may be configured such that the hook head defines a space, e.g., between the trough of the recess 20 and the spacing region 21a when the snare 15 is retracted to a first retracted position (see, e.g., FIG. 22A), thereby permitting/enabling suture slide. In some embodiments, the snare 15 may then be further retracted to a second retracted position (not shown), e.g., thereby creating a clamping effect between the spacing region 21a and the recess 20.

Figure 20D:
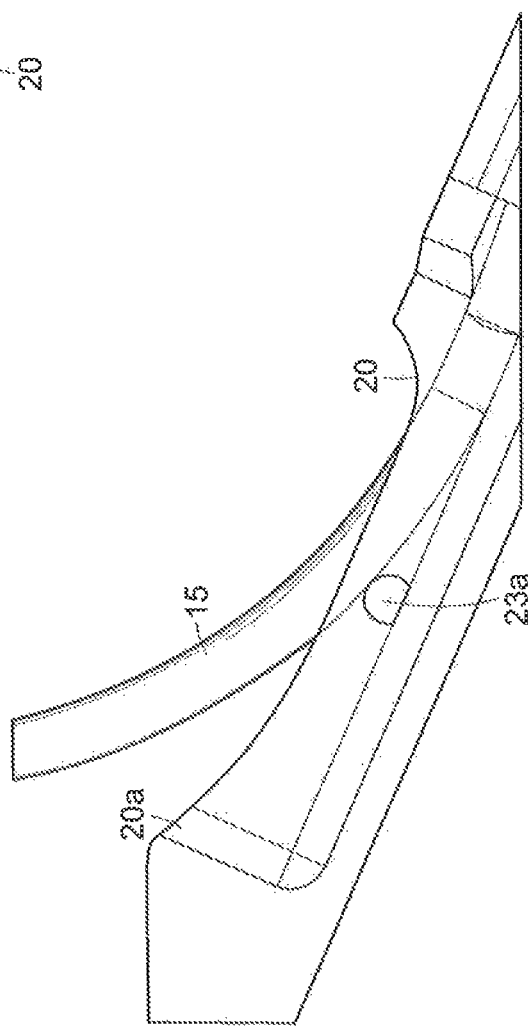

As depicted in FIGS. 20A-20D the exit position of the snare 15 of FIGS. 19A-19C (e.g., in the open and/or closed positions, as impacted by the length of the slot 23a, angle of the shaft 11 relative to a needle tip 14, shape of the needle tip 14, distal shape of the snare 15 and/or the pre-bend of the snare 15) may be important. For example, as depicted in FIGS. 20A-20C, a slot 23a that has too much length, a snare 15 that has too much bend, a shaft 11 that has to much curve/angle or other similar factors may cause the snare to exit at a position that is too far proximal, creating a space 23c between the shaft 11 and the elongated region 21a of the hook head 21 snare 15 and potentially leading cleating of a suture S (see, e.g., FIG. 20C). FIGS. 20A-20C depict that an example slot 23a extends too far proximal in the device. When the snare 15 is in the closed position, a gap 23c is created that lends itself to suture cleating as shown in FIG. 20B. FIG. 20c shows and example of the suture S being cleated in the gap 23c. Thus, in example embodiments it may be advantageous have the length of the slot 23a limited to the diameter of the snare 15 at the exit point from the shaft 11 (or utilize another configuration that allows the snare distal geometry 21, 21a, 22 to mate correctly with the needle tip slot geometry such that suture is not susceptible to cleating). In some embodiments, the slot 23a may be angled similar to the angling of the side channel in previous embodiments. Thus, the length of the slot may increase (e.g., in a graduated manner) from the outer wall of the shaft 11 to the lumen of the shaft). This may help reduce any high stress interactions between the snare pre-bend and needle tip slot.

As depicted in FIG. 20D, a similar problem of cleating may be caused by the exit point being too far distal, e.g., close to the distal lip 20a of the recess 20, and/or by the snare 15 not providing enough of an angle or clearance relative to the trough of recess 20. Thus, e.g., a biasing element 23d (e.g., a wedge) may be included for improving clearance and preventing the exit point from being too far distal. The cleating issue in FIG. 20D may arise after a suture is contained in the device, and the device is passed through tissue with the hook in the closed position. When residual proximal tension maintained on the suture by the pierced tissue, and the snare is extended to the open position, the pre-bend section of the snare can ride over the suture itself (as the suture cannot move distal due to proximal tension applied by the tissue). At this point, the suture would may be cleated in between the pre-bend of the snare and the slot of the needle tip.

Figure 21:
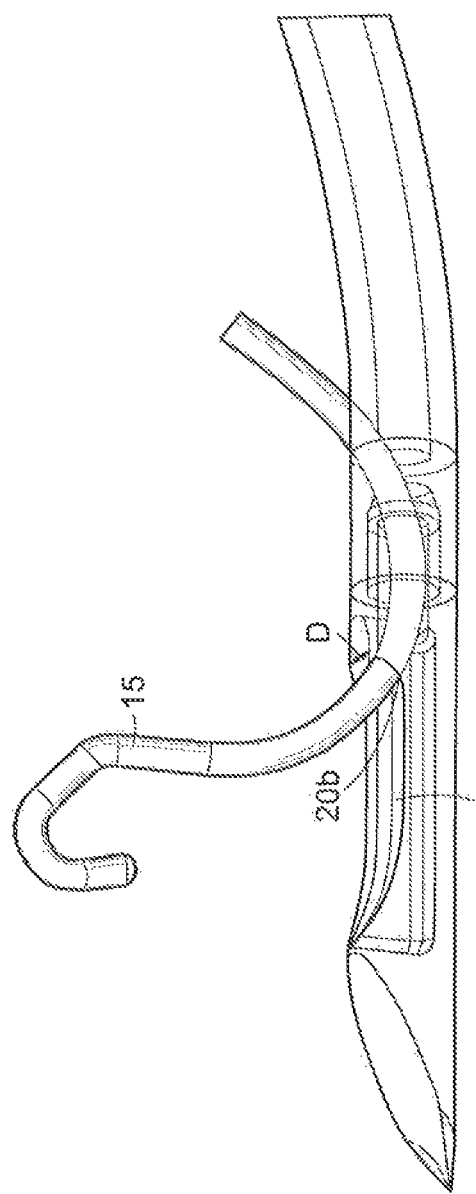
FIG. 21 illustrates an example use of side walls of a slot in a distal end of a distal curved region of a shaft of an example suture passer instrument to constrain/align the planer orientation of a snare with a pre-bend relative to a needle tip, according to the present disclosure.

FIG. 21 illustrates, with respect to the embodiment of FIGS. 19A-19C, how the width D, of the slot 23a as well as the width of the side walls of the recess 20 (particularly at a proximal lip 20b of the recess 20) may be configured so as to exhibit a narrow tolerance relative to snare 15, thereby preventing/resisting rotation of the suture snare (e.g., by biasing the pre-bend of the snare 15 to remain in plane with the walls of the recess 20 and slot 23a). In example embodiments the walls side walls of the slot and/or recess may be substantially parallel to one another.

Figure 22B:
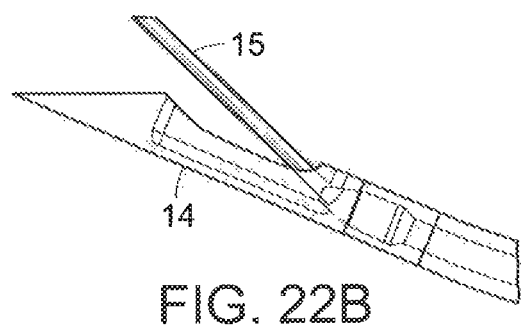
Figure 22C:
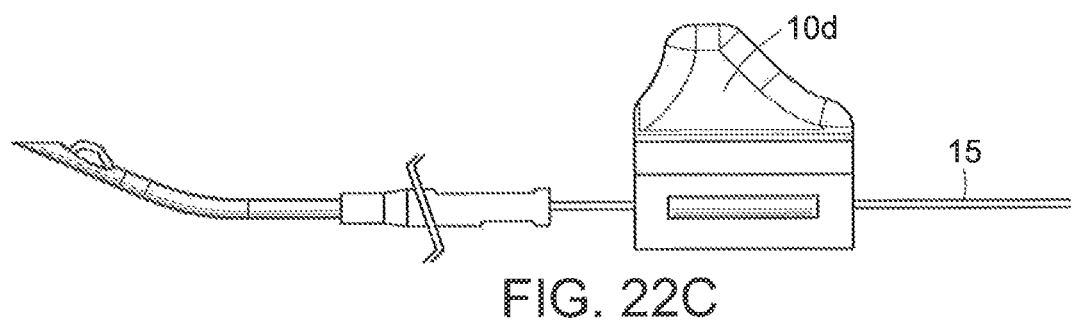
Figure 22D:
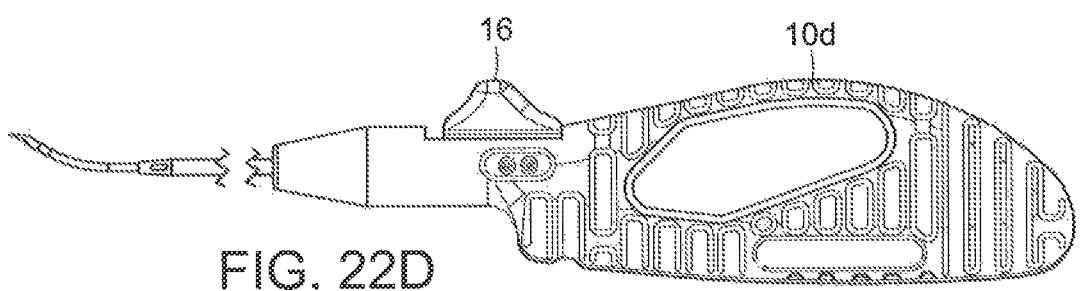

With reference now to FIGS. 22A-22D an example manufacturing process for manufacturing example suture passer instruments (such as disclosed herein) is represented. With initial reference to FIG. 22A the shaft and needle tip of a suture passer instrument 10 may be assembled by securing together, e.g., welding together three components 10a, 10b and 10c. The distal component 10a may advantageously define the needle tip geometry (e.g., alignment, size and/or shape of the needle tip, configuration of the recess, etc.), as well as the geometry of a distal end of the shaft, (e.g., geometry of any side channel or slot, geometry of a bent distal region of the shaft, etc.). The middle component 10b may define the geometry of a middle portion of the shaft including, e.g., for any distal or medial curved region thereof. Lastly, the proximal component 10c may define a proximal geometry the shaft including, e.g., for a proximal elongated straight region thereof. The proximal component may also define one or more interface features for interfacing with a handle component. Advantageously, individual components types 10a, 10b and 10c may be manufactured in bulk and then mixed and matched to produce many different configurations of the suture passer instrument 10. In some embodiments, this may enable providing a suture passer instrument 10 with interchangeable components. As depicted in FIG. 22B, once the components 10a, 10b and 10c are assembled together the snare 15 may be threaded through the lumen from the distal end near the needle tip 14. As described herein, the snare 15 may be of any number of different geometries/configurations (thus the snare 15 may likewise be a configurable or interchangeable component of the suture passer instrument 10. As depicted in FIGS. 22C and 22D, once the snare is threaded through the lumen, a handle component 10d may be secured. In example embodiments, such as depicted in FIG. 22C, the handle component 10d may be secured directly to the snare 15 thereby enabling manual manipulation thereof (e.g., by sliding the handle component 10d and snare 15 relative to components 10a-c). Alternatively, as depicted in FIG. 22C, the handle component 10d may be secured relative to the proximal component 10c, e.g., wherein a button 16 may be used to manipulate the snare. In further example embodiments, the handle component may include automated/powered actuation of the snare. In some embodiments, the handle component may include one or more stops for assessing, locking, or otherwise controlling the position of the snare (for example, the handle may define a first stop for a first retracted position providing for suture slide and a second stop for a second retracted position for clamping the suture). In some embodiments, a snare may be configured to include multiple hook ends. In further embodiments, suture passer instrument 10 may include a plurality of lumens (e.g., operatively associated with opposite sides of a dual canulated needle tip). In some embodiments, the suture passer instrument 10 may be configured to provide sufficient clearance/space (e.g., approximately 0.018-0.036 inches perpendicular to the needle tip axis and 0.042-0.122 inches in a direction parallel to the needle tip axis for a size 2 suture) to allow for suture slide, e.g., when the snare is in a first retracted position (see, e.g., FIG. 10a). In example embodiments, clearance between the diameter of the snare and the lumen and/or a cannulation of the needle tip may be between 0.007-0.012 inches or greater (particularly, in the direction of the pre-bend). In example embodiments, clearance between the side walls of the recess and/or the slot may be substantially less (e.g., between 0.002 and 0.006 inches). In example embodiments, the side walls of the recess and/or the slot may be angled to provide off plane (e.g., relative to the curve of the shaft, and or relative to the plane perpendicular to the tapered plane of the needle tip) orientations of the snare.

Figure 23:
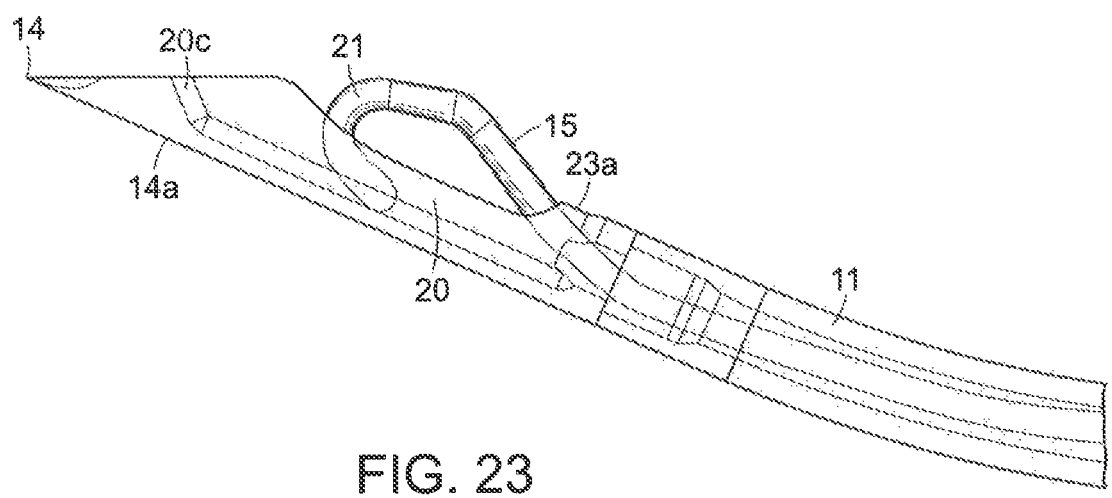
FIG. 23 illustrates a side view of a further example embodiment of a distal end of a suture passer instrument, the example embodiment illustrating an angled distal side wall of a recess defined in a needle tip of the suture passer instrument, according to the present disclosure.

With reference now to FIG. 23 a further example embodiment of a distal end of a suture passer instrument is depicted. The embodiment of FIG. 23 is similar to the embodiment of FIGS. 19A-19C and includes a slot 23a defined in the side wall of the shaft 11 that flows directly into the trough of the recess 20. As noted herein, the recess 20 may or may not extend through a distal end of the needle tip 14. Preferably, the recess 20 does not extend all the way through the distal end and sharp portion of the needle tip but rather terminates at an end wall 20c, e.g. which, as depicted in FIG. 23, may exit the needle tip 14 at approximately a 45 degree angle from the edge 14a of the needle tip. This distally angled slot portion of the recess 20 may advantageously ensure that the hook head is not able to be pulled such that the distal hook end 21 of the snare 15 is wedged or otherwise catches with respect to the recess 20. The angled slot portion may also facilitate a kick out trajectory and/or orientation of the snare 15.

These and other features and characteristics, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of claims.

The invention claimed is:

1. A surgical instrument comprising:
a shaft, comprising a tubular member having a proximal end and a distal end, a lumen extending between the proximal and distal ends, and a tip distal to the tubular member, the tip including a recess defining a trough cutout into a sidewall of the shaft, the trough having a first width defined by two diagonal sidewalls cut into the sidewall of the shaft to define a bottom of the trough and an area where a portion of the shaft sidewall is missing, the diagonal sidewalls running parallel to a length of the shaft; and a handle connected to the proximal end of the shaft;

wherein the shaft includes a distal portion having an opening in the sidewall thereof, proximal to the tip, the opening in communication with the lumen through a slot in the sidewall adjacent to the opening, the slot having sidewalls forming a second width in a circumference of the sidewall of the shaft;

wherein the instrument further comprises a suture snare, the snare being slidably receivable within the lumen and the slot, and movable through the slot between extended and retracted positions for capturing the suture, the snare including a pre-bend; and wherein the first width and the second width each have a narrow tolerance relative to the snare and the bottom of the trough is on a distal side of the shaft and the slot is on a proximal side of the shaft, the proximal side being opposite the distal side with respect to the circumference of the shaft to bias the pre-bend of the snare to remain in a plane with the sidewalls of the slot and the sidewalls of the recess to prevent the snare from rotating.

2. An instrument according to claim 1, wherein the distal portion of the shaft is curved.

3. An instrument according to claim 2, wherein the opening is located on an outside diameter of the distal portion.

4. An instrument according to claim 1, wherein the snare includes a distal hook.

5. An instrument according to claim 4, wherein the recess is adjacent to and distal of the opening.

6. An instrument according to claim 5, wherein the recess houses the distal hook when the suture snare is in the retracted position.

7. An instrument according to claim 1, wherein the suture snare is further configured to pass through the slot in the extended position to capture the suture.

8. An instrument according to claim 1, wherein the lumen has a stepped inner diameter and includes two or more sections having different diameters.

* * * * *